United States Patent [19]

Petrofsky

[11] Patent Number: 4,642,769
[45] Date of Patent: Feb. 10, 1987

[54] METHOD AND APPARATUS FOR PROVIDING STIMULATED EXERCISE OF PARALYZED LIMBS

[75] Inventor: Jerrold S. Petrofsky, Beavercreek, Ohio

[73] Assignee: Wright State University, Dayton, Ohio

[21] Appl. No.: 722,249

[22] Filed: Apr. 11, 1985

Related U.S. Application Data

[63] Continuation-in-part of Ser. No. 503,103, Jun. 10, 1983, abandoned.

[51] Int. Cl.⁴ .............................................. G06F 15/42
[52] U.S. Cl. ..................................... 364/415; 364/413; 272/DIG. 6; 128/419 R; 128/421; 128/423 W
[58] Field of Search ........ 364/413, 415, 417, 550–551, 364/200 MS File, 900 MS File, 300; 272/116–118, 129, DIG. 6; 128/423 W, 419 R, 421, 689, 783, 795–796

[56] References Cited

U.S. PATENT DOCUMENTS

| | | | |
|---|---|---|---|
| 3,845,756 | 11/1974 | Olsson | 128/2.06 R |
| 4,235,437 | 11/1980 | Ruis et al. | 272/134 |
| 4,244,021 | 1/1981 | Chiles, III | 364/413 |
| 4,278,095 | 7/1981 | Lapeyre | 128/689 |
| 4,281,663 | 8/1981 | Pringle | 128/689 |
| 4,480,830 | 11/1984 | Petrofsky et al. | 272/117 |
| 4,499,900 | 2/1985 | Petrofsky et al. | 128/423 |

FOREIGN PATENT DOCUMENTS 2822343 11/1979 Fed. Rep. of Germany ...... 272/129

OTHER PUBLICATIONS

H. Gernsback, "Electronics and the Aged", *Radio-Electronics*, vol. 36, No. 6, Jun. 1965, p. 29.

*Primary Examiner*—Gary V. Harkcom
*Attorney, Agent, or Firm*—Biebel, French & Nauman

[57] ABSTRACT

A computer control system which allows precise control of movement in paralyzed muscle through functional electrical stimulation. The system includes a computer operated at a programming center under physician control, an electronically erasable and programmable read only memory removable cartridge and a remotely located second computer for controlling the operation of appropriately configured exercise equipment. By using this system, a physician can set work limits for a patient, and the patient can then exercise essentially under a physician's control but without the physician's direct and continuous supervision. In a preferred embodiment, records of the intensity and length of the workout are kept on the cartridge so that the physician can recall the data and get a graphical printout from the computer.

12 Claims, 19 Drawing Figures

METHOD AND APPARATUS FOR PROVIDING STIMULATED EXERCISE OF PARALYZED LIMBS

CROSS REFERENCE TO RELATED APPLICATION

This application is a continuation-in-part of Ser. No. 503,103, filed June 10, 1983 and now abandoned.

BACKGROUND OF THE INVENTION

The present invention relates to methods and apparatuses for electrically stimulating muscles and, more particularly, to a computer controlled system and method for exercising paralyzed muscles through programmed electrical stimulation.

Each year thousands of persons are permanently paralyzed as a result of traumas sustained by their spinal cords. Often, the trauma is such that there is no direct damage to most of the muscles in the victim's body, but communication between brain and the lower spinal cord is eliminated, which results in a permanent loss of control of certain muscle groups. This loss of control causes a number of additional problems in the body of the victim. The first of these is the atrophy of the uncontrolled muscle from disuse. Disuse atrophy is distinguishable from other types of atrophy in that the muscle and associated tendons are still functionally healthy, but because of lack of use, the muscle wastes away and loses much of its protein content.

A second problem is demineralization of the bones associated with the uncontrolled muscles due to the lack of muscle activity. After bone demineralization has become advanced, the simple act of passively moving the leg of a victim can break a bone or crack a joint. In addition, deterioration of the tendons and other soft tissue occurs, as well as a severe wasting away of cardiac tissue. The latter results in a compromised cardiovascular system which predisposes the victim's body to secondary cardiovascular disease and secondary renal disease. All of these conditions are commonly found in the pathology of victims of spinal cord injury after chronic paralysis.

Until recently it was believed that a spinal cord injury could not be cured. Consequently very little was done for persons having spinal cord injury aside from trying to maintain their bodily health. However, recent advances in spinal cord research have given new hope to those who are paralyzed due to spinal injury. Furthermore, techniques have now been developed for causing movement of a victim's hands or legs, through functional electrical stimulation. This latter development makes it possible to exercise paralyzed limbs and keep them in good physical condition. Hopefully such conditioning will enable restoration of useful functional activity when a cure for spinal cord injury has been developed. Such conditioning also helps to reverse or eliminate the secondary diseases associated with spinal cord injury. Elimination or reversal of these diseases may greatly reduce medical costs and increase the longevity of the spinal injury victim.

Examples of systems for exercising paralyzed limbs through functional electrical stimulation may be found in Petrofsky et al U.S. Pat. Nos. 4,480,830 and 4,499,900, the disclosures of which are incorporated herein by reference. Such systems can work the muscles to precise levels and increase the metabolic loads as appropriate to produce muscle build-up. With these exercise systems it is possible to bring the muscle back to normal strength and to retrain the cardiovascular system. However, the health of the patient requires that the program be carried out progressively under the direction of an attending physician. During the course of the program it is important that limits be set on the work load and on physiological parameters such as body temperatures, heart rate and blood pressure. The exercise system must include means for measuring such variables, and provision must be made for terminating an exercise routine whenever one of the prescribed limits has been exceeded. If the physician is not present during the exercise, then provision must be made for generating a report of the performance of the patient during the routine, so that the prescribed limits may be appropriately adjusted.

SUMMARY OF THE INVENTION

The present invention improves the system disclosed in the aforementioned Petrofsky et al applications by providing an electronic "prescription" system for controlling stimulated exercise of paralyzed limbs. In accordance with the practice of the invention, workload limits for the paralyzed muscles of a subject may be set under the direction of an attending physician. These limits may include the maximum weight to be moved by the limb, maximum heart rate, maximum systolic blood pressure, maximum diastolic blood pressure, maximum body temperature and maximum number of limb movement cycles. Heart rate, blood pressure and body temperature may be specified for resting and for exercise conditions.

The above-noted exercise parameters are stored in an electronically programmable memory cartridge by a computer operated under physician control. This cartridge is given to the patient who takes it to a location equipped with a computer controlled exercise system. This system reads the information on the cartridge and uses it for control of a programmed routine of stimulated exercise. Exercise is automatically terminated whenever any of the prescribed conditions are exceeded. The cartridge may be reused a limited number of times as determined by usage limit information which the physician may cause to be stored within the cartridge.

Upon termination of an exercise session the exercise system records all physiological parameters which have been specified by the physician and stores them in the cartridge. After a cartridge has been used the prescribed number of times, the patient returns it to the physician. The data which is stored on the cartridge is read out by the physician's computer for use in prescribing the further course of the stimulated exercise. In this way the physician can direct a gradual build-up of the muscles under precisely controlled conditions.

Accordingly, it is an object of the invention to provide a method of physician-controlled stimulated exercise of paralyzed limbs.

It is another object of the invention to provide an improved system for carrying out stimulated exercise of paralyzed limbs.

Other objects and advantages of the invention will be apparent from the following description, the accompanying drawings and the appended claims.

DESCRIPTION OF THE PREFERRED EMBODIMENT

Figure 1:
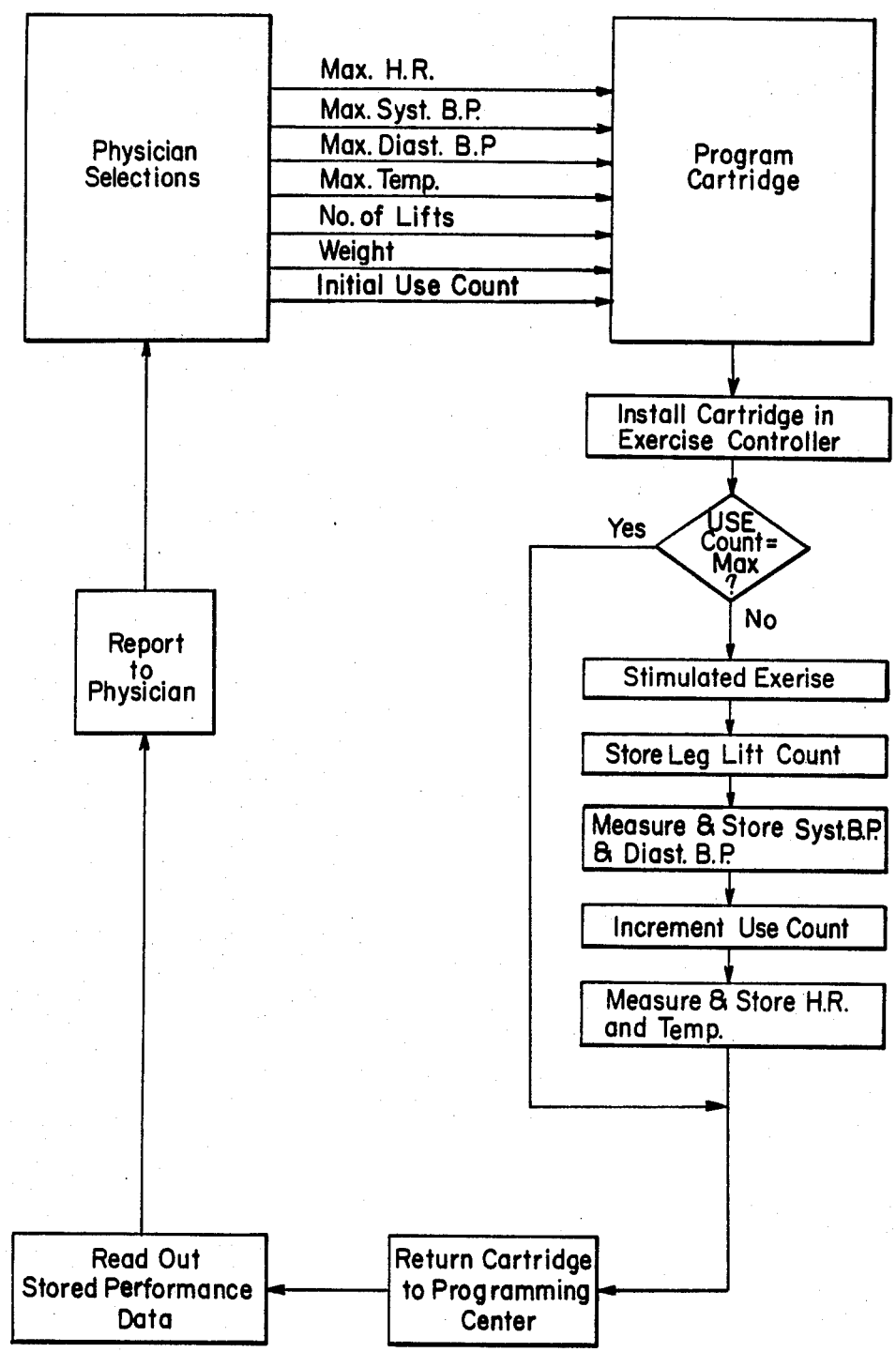
FIG. 1 is a flow chart for a program of stimulated exercise carried out in accordance with this invention.

A program of electrically stimulated exercise for a paralyzed person may be established and implemented as generally illustrated by the block diagram of FIG. 1. Accordingly, an attending physician may write a prescription establishing an exercise routine, such as leg lifting or exercycle pedaling, including a set of parameters controlling the nature of the exercise and physiological response limits to be observed. These parameters are stored in a memory cartridge which may comprise an electronically erasable and programmable read only memory, commonly known as EEPROM. Data representing the control parameters may be "burned" into the EEPROM by a suitably programmed computer, as hereinafter described. Preferably, the computer is located in the physician's office and operated by him or personnel under his control.

After the cartridge has been loaded with the appropriate data it is given to the patient, who takes it to a place equipped with apparatus for carrying the prescribed exercise program. This equipment may include an exercycle system of the type generally disclosed in Petrofsky et al U.S. Pat. No. 4,499,900 and an exercise chair as disclosed in Petrofsky et al U.S. Pat. No. 4,480,830. For purposes of this description it will be assumed that the physician has prescribed exercise in an exercise chair. Reference may be made to U.S. Pat. No. 4,499,900 for background information to enable application of the invention to an exercycle. Furthermore, the invention may be used for exercising paralyzed arms through use of a stimulation system of the type described in Petrofsky U.S. Pat. No. 4,558,704.

When prescribing leg exercise the physician may prescribe the weight to be lifted and the maximum number of leg lifts. Other parameters which may be prescribed are the maximum body temperature (at rest and during exercise), maximum diastolic blood pressure (at rest and during exercise), maximum systolic blood pressure (at rest and during exercise) and maximum heart rate (at rest and during exercise). It will be appreciated that only one of the prescribed limits will be reached during an exercise routine. The system affords the physician the flexibility of choosing one parameter as an instrument of exercise control and selecting appropriate values of other parameters to maximize the safety of the procedure.

It has been observed that the endurance of a paralyzed person rapidly increases during the course of a program of stimulated exercise. Accordingly, the physician will want to review the patient's progress from time to time and make appropriate adjustments in the prescribed exercise parameters. For this reason a memory location is reserved in the cartridge for storage of a number indicating the number of cartridge uses. When the EEPROM is programmed at the physician's office, an initializing count (which may be 0000) is stored in that memory location. That number is incremented each time the cartridge is used. After a predetermined maximum count has been reached, further cartridge use is prevented.

Typically, the physician will desire that the patient exercise both legs, so a cartridge will be prepared for each leg. Each cartridge will be loaded with data for controlling the exercise routine as well as the number of cartridge uses. A written prescription may be prepared on an adhesively backed blank and secured on the side of one of the cartridges. The written prescription may document the data loaded into the cartridge and present any additional special instructions such as the muscles to be stimulated, the type of equipment to be used, etc.

When the patient reports to the exercise center the cartridge is installed in the exercise controller for checking of the use count. Thereafter (assuming that leg lifts have been prescribed) stimulated leg lifting is begun on one leg. Prior to and during the course of the exercise the patient's blood pressure (both systolic and diastolic), heart rate and body temperature are monitored automatically. Leg lifting continues until a prescribed physiological parameter has been exceeded or until the predetermined maximum number of leg lifts have been reached. Thereafter the exercise routine for the first leg is terminated, and final measurements of the prescribed physiological parameters are made. Measurement data, together with the leg lift count are stored on the cartridge in specially reserved memory locations. At this time the exercise controller increments the number in that storage location within the cartridge which carries the use count.

After one leg has been exercised, the patient is rested and the entire procedure is repeated for the second leg. The second routine is carried out using the above-mentioned second cartridge, which may, if desired, be programmed differently than the first cartridge. The entire procedure may be repeated on subsequent visits to the exercise center until predetermined maximum usage counts on the cartridges have been reached.

When the cartridges have been used the maximum number of times they are returned by the patient to the programming center, which as noted above, is preferably located at the physician's office. The program which is used for loading exercise control information into the cartridge is provided with a special routine for reading out data stored therein at the exercise center. The data so read out is reported to the physician for use in prescribing the further course of the patient's exercise.

Figure 2:
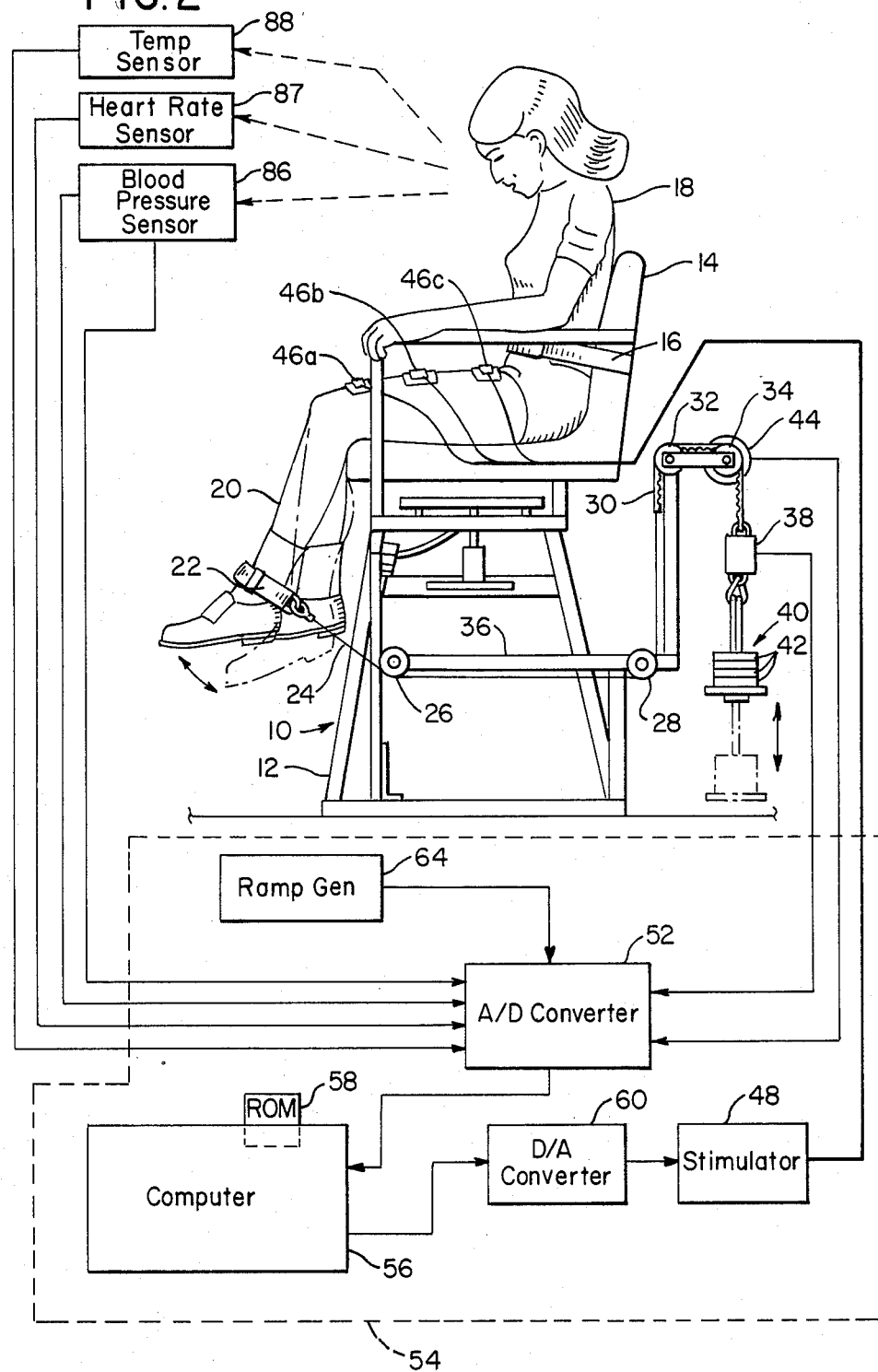
FIG. 2 is a somewhat schematic side view of an exercise system for conducting stimulated exercise in accordance with the flow chart of FIG. 1.

As shown in FIG. 2, an exercise system, generally designated 10, comprises a frame 12 which supports a chair 14 having straps 16 and which is adapted for comfortably supporting a patient 18. The lower portion of the left leg 20 of the patient is enclosed by an adjustable strap 22 attached to a cable 24. The cable 24 is entrained about pulleys 25, 28 and is connected at an opposite end thereof to timing belt 30.

Timing belt 30 is entrained about pulley 32 and pinion gear 34 such that displacement of the timing belt positively drives the gear 34. The pulleys 26, 28 supporting the cable 24, as well as the pulley 32 and gear 34 supporting the timing belt 30, are mounted on the frame 12 by a support structure 36.

An end of the timing belt 30 opposite the end attached to the cable 24 is attached to a load cell 38 of well-known design. A weight 40 is suspended from the load cell 38, and comprises a plurality of plates 42 so that the total resistance provided by the weight 40 can be varied to provide the prescribed weight. Thus, extension of the leg 20 causes the weight to be raised; the weight providing a substantially constant resistance throughout the limited range of movement indicated in FIG. 1.

The gear 34 is attached to a potentiometer 44 which generates a signal proportional to the displacement of the belt 30 (and the extension of leg 20). Electrodes 46a, b, c, are attached to the skin of the leg 20 above the muscles to be stimulated and are connected to a stimulator 48 by wires 50. The potentiometer 44 and load cell 38 are connected to an analog-to-digital converter 52. Also connected to analog-to-digital converter 52 are a ramp generator 64, a body temperature sensor 88, a heart rate sensor 87 and a blood pressure sensor 86.

Figure 9A:
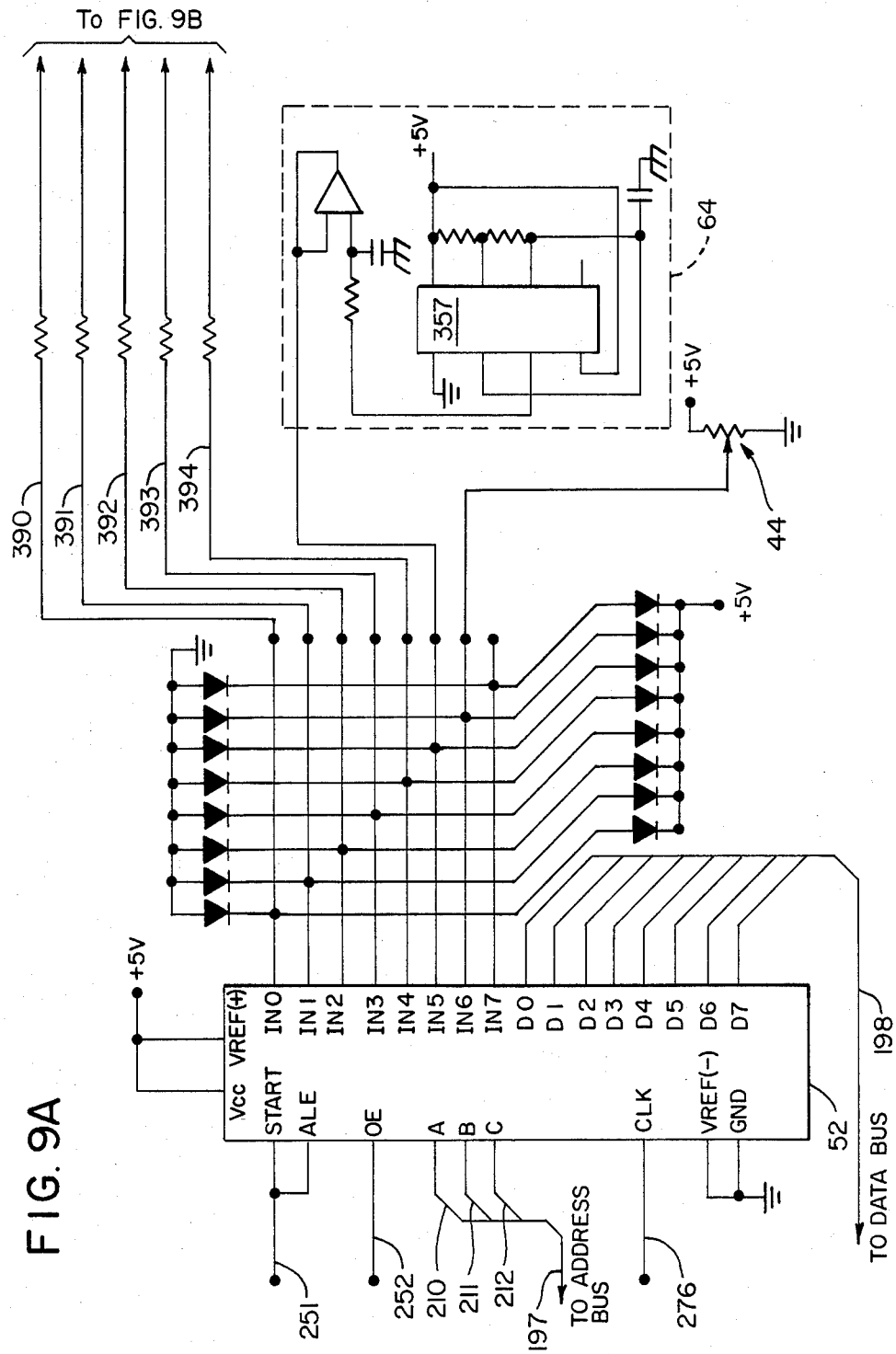
FIGS. 9A and 9B are a schematic diagram of a sensing system for the microprocessor of FIGS. 6A and 6B.
Figure 9B:
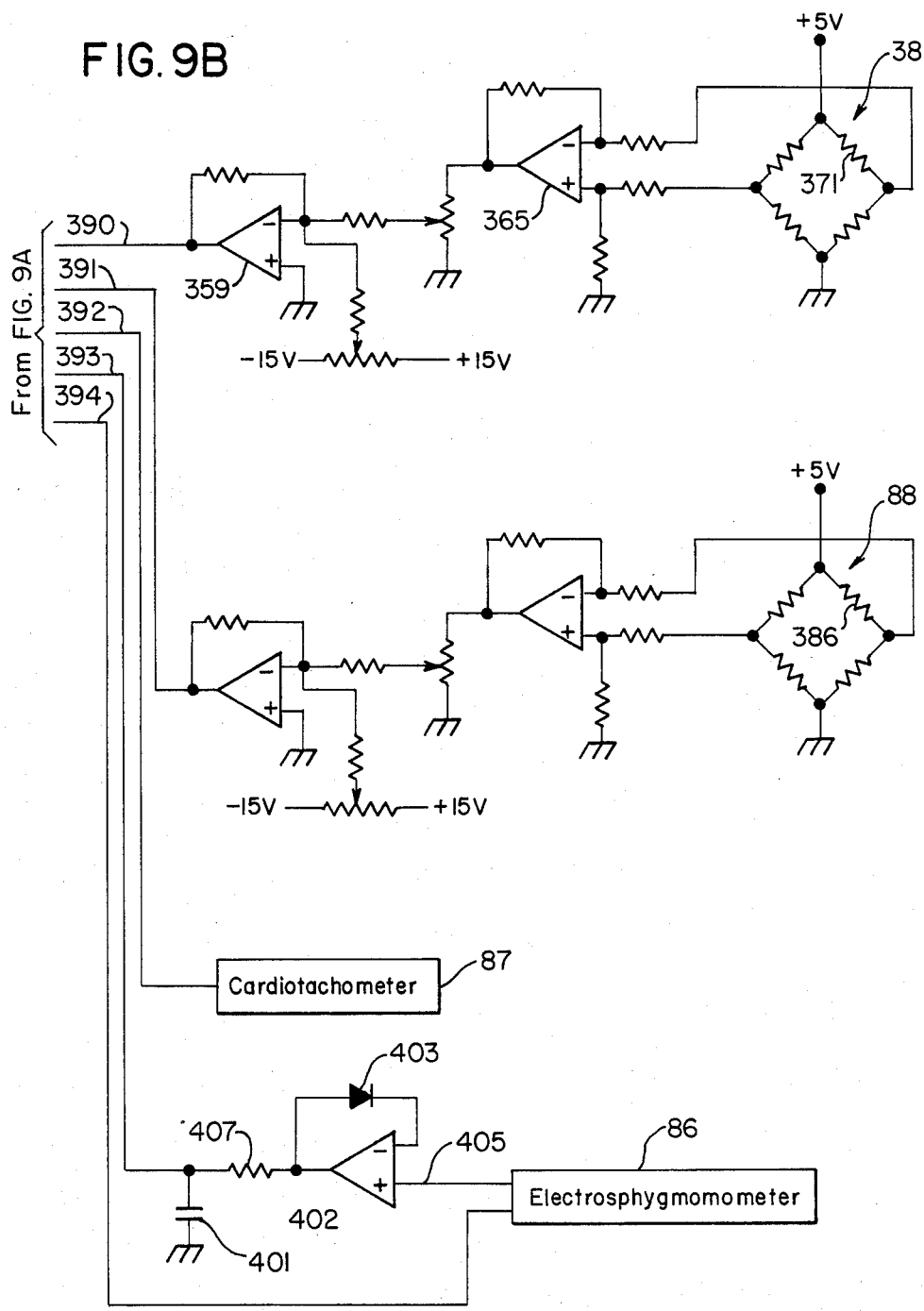

Ramp generator 64 generates a triangular wave form which is used as a reference signal for feedback control of leg stimulation, as more fully described in Petrofsky et al Ser. No. 417,935. Blood pressure sensor 86 may be a Copal digital sphygmomometer Model UA-251 which provides two outputs utilized as hereinafter described for calculating systolic blood pressure and diastolic blood pressure. Heart rate sensor 87 may be a cardiotachometer Model CT-2 manufactured by Gedco Associates, Inc. Temperature sensor 88 may comprise a thermister 386 mounted in a bridge circuit as generally illustrated in FIG. 9B.

Figure 6A:
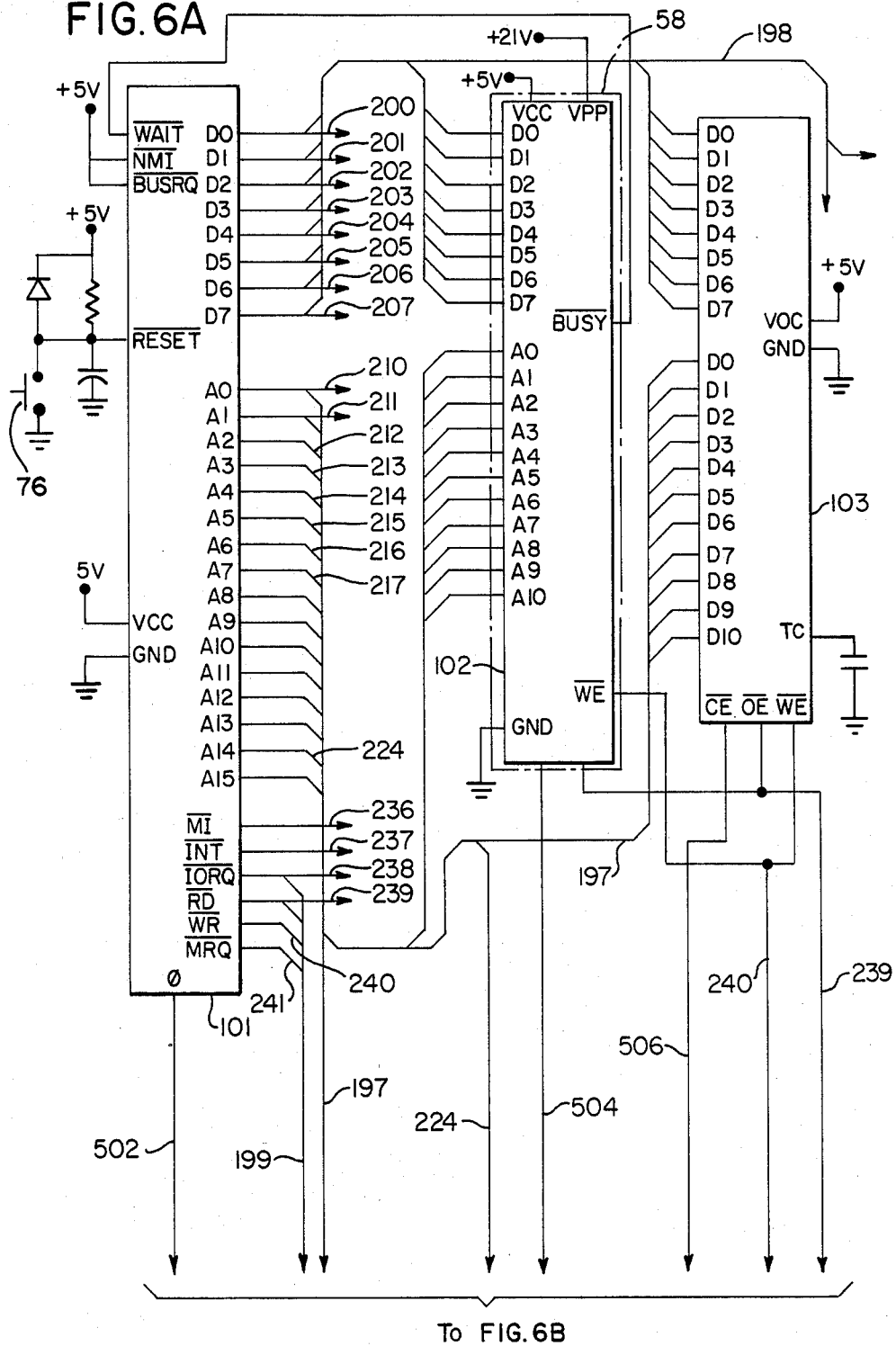
FIGS. 6A and 6B are an electrical schematic diagram for a microprocessor system to carry out the program of FIGS. 4A-4D and 5.
Figure 6B:
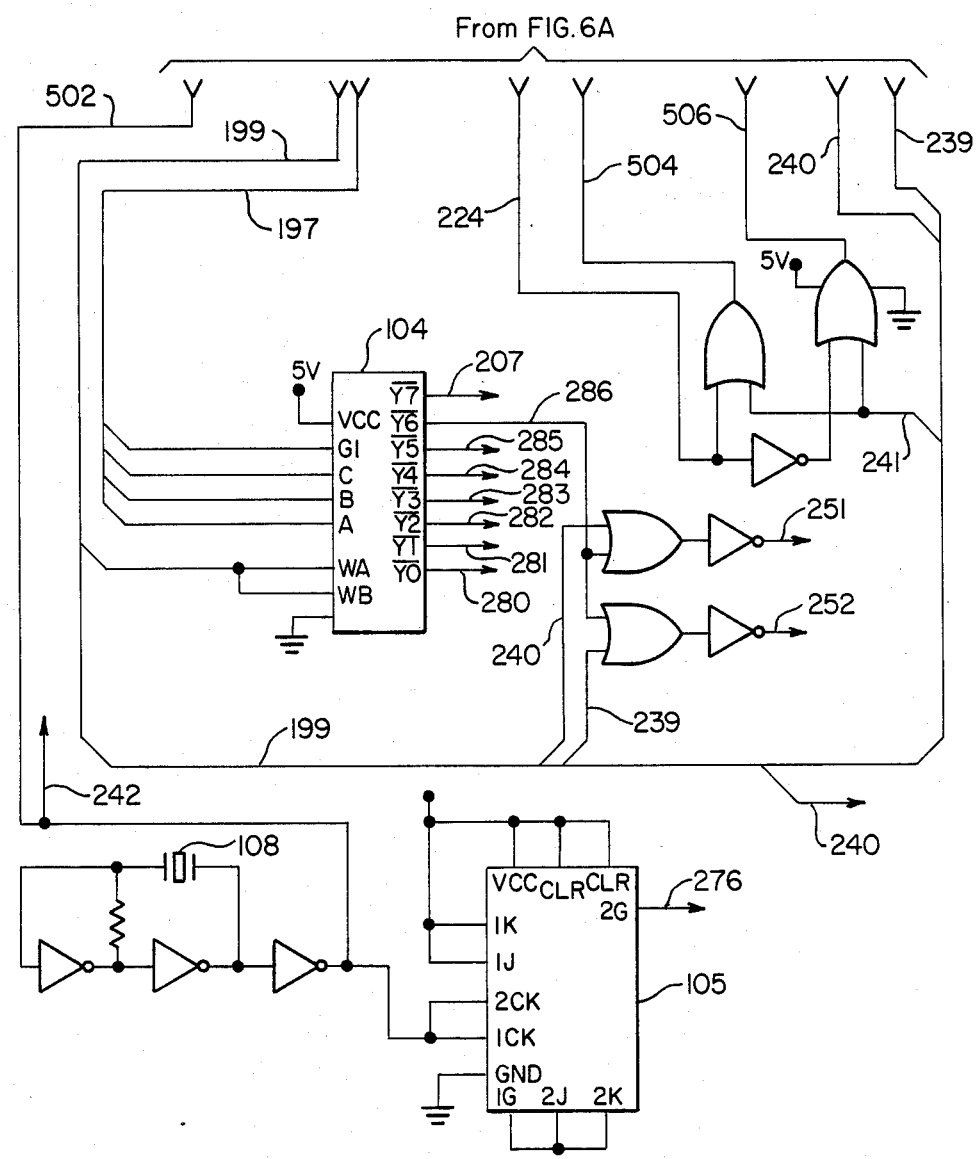
Figure 7:
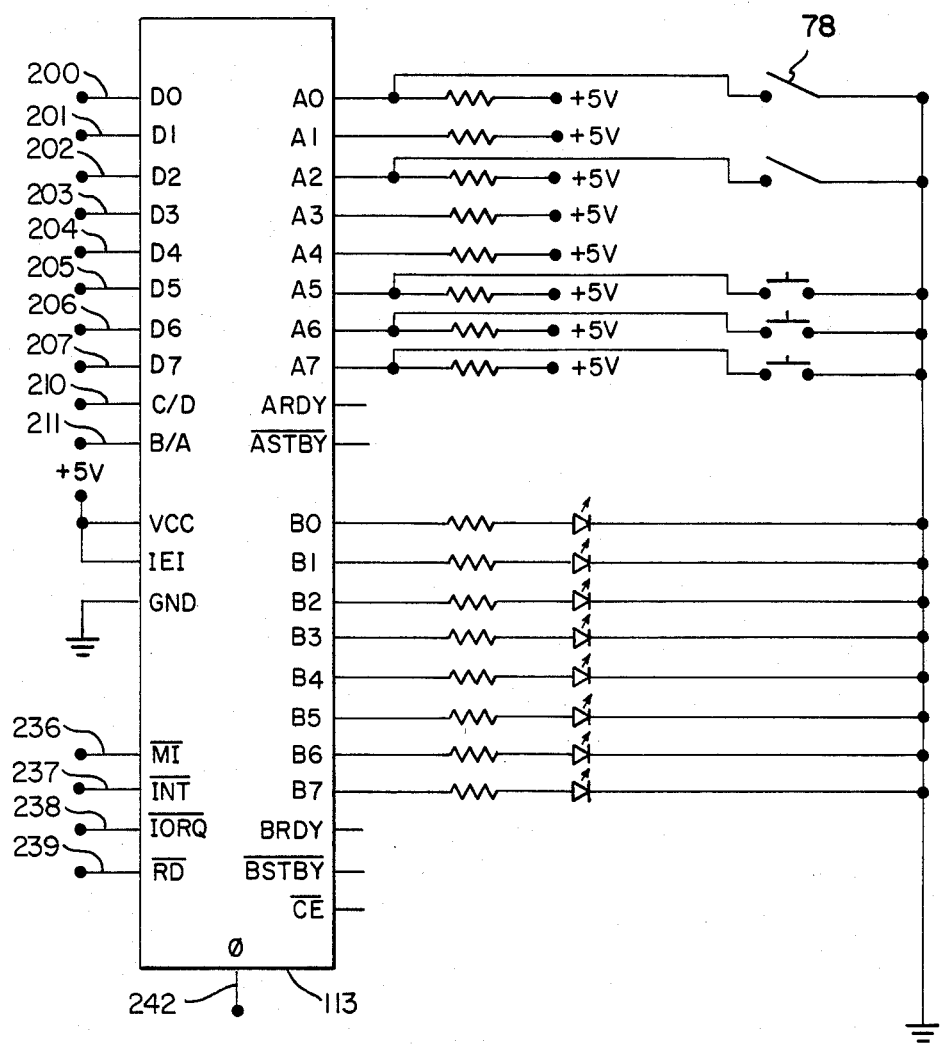
FIG. 7 is a schematic diagram of a parallel input/out port interfaced with the microprocessor system of FIGS. 6A and 6B.
Figure 8:
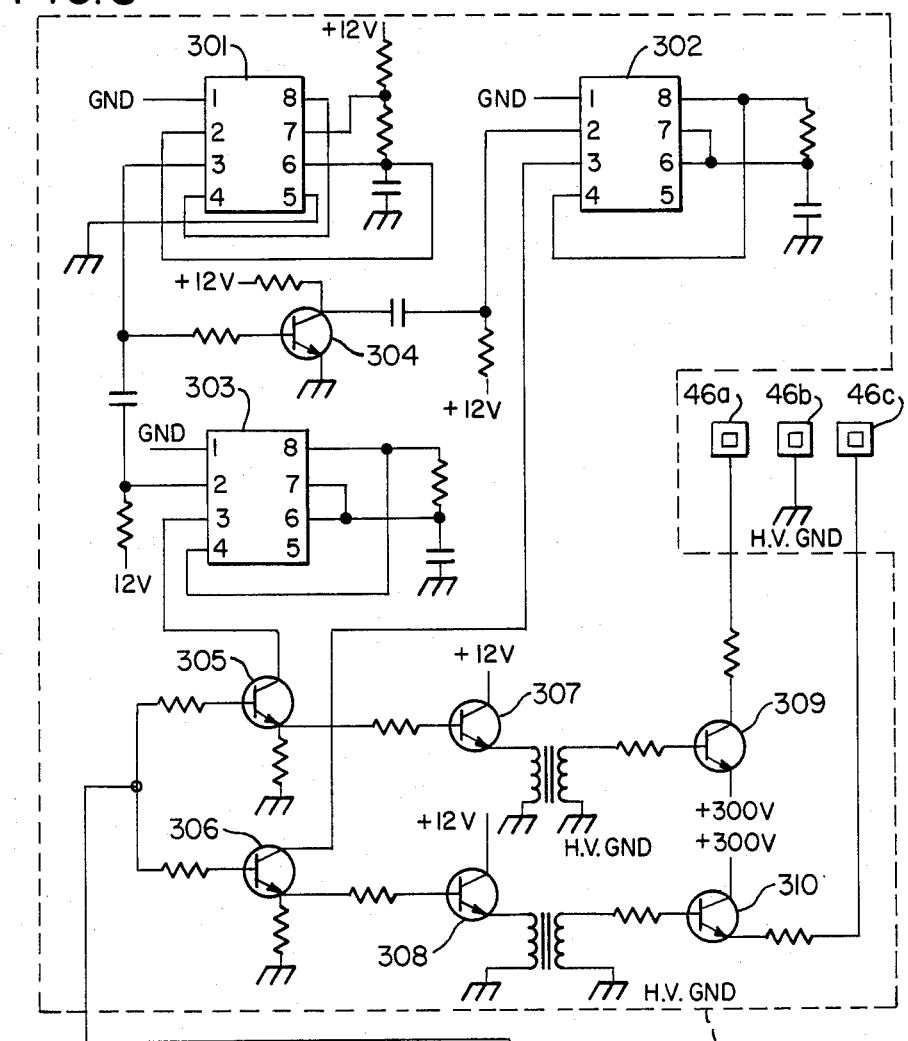
FIG. 8 is a schematic diagram of a muscle stimulator and a digital-to-analog converter connected thereto.
Figure 8:
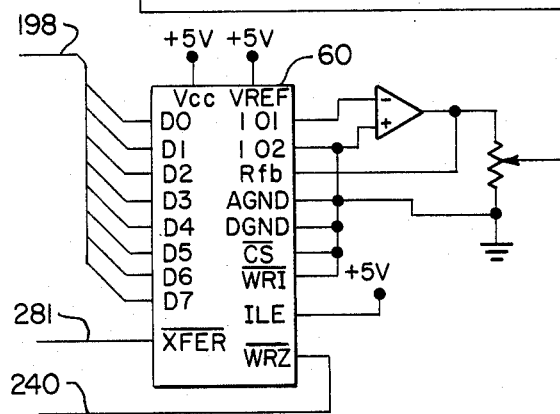

Digitized output signals from A/D converter 52 are provided to computer 56 which may be configured as generally illustrated in FIGS. 6A, 6B and 7. The heart of computer 56 is a Z80 integrated circuit microprocessor designed and manufactured by Zilog, Inc. of Cupertino, Calif. Computer 56 is provided with a connector for reception of a memory cartridge 58 carrying exercise control information stored therein as described above. Computer 56 generates stimulation control signals in a digital format for application to a digital-to-analog converter 60. D/A 60 converts the digital signals to analog format and supplies them to stimulator 48, as illustrated in FIG. 2. A schematic diagram illustrating the details of D/A converters 60 and stimulator 48 is presented in FIG. 8. FIGS. 9A and 9B present schematic details for A/D converter 52, ramp generator 64, blood pressure sensor 86, heart rate sensor 87 and temperature sensor 88. For further description of the control of a muscle stimulation system by a Z80 microprocessor, reference may be made to Ser. No. 561,720.

Figure 3:
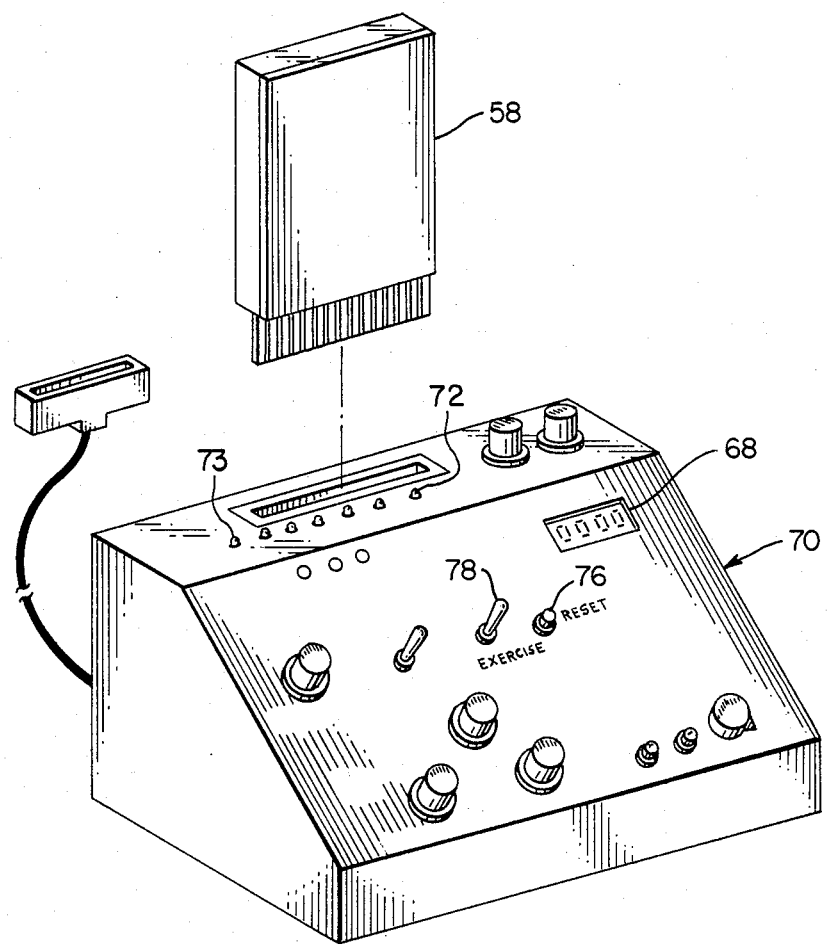
FIG. 3 is a perspective view of a control console for the exercise system of FIG. 2.
Figure 4A:
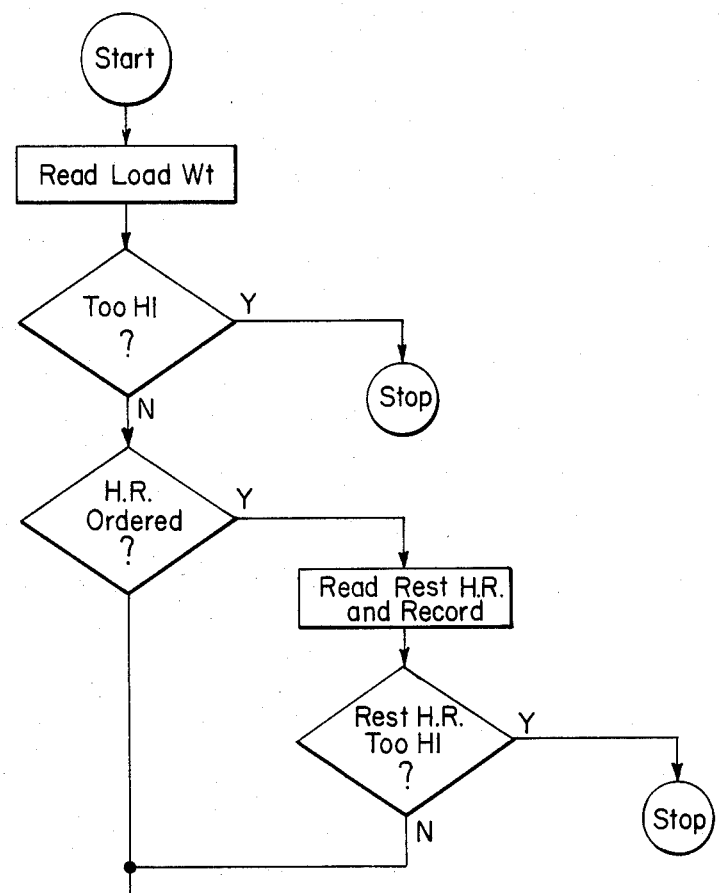
FIGS. 4A-4D are a flow chart for a computer program to control the exercise system of FIG. 2.
Figure 4B:
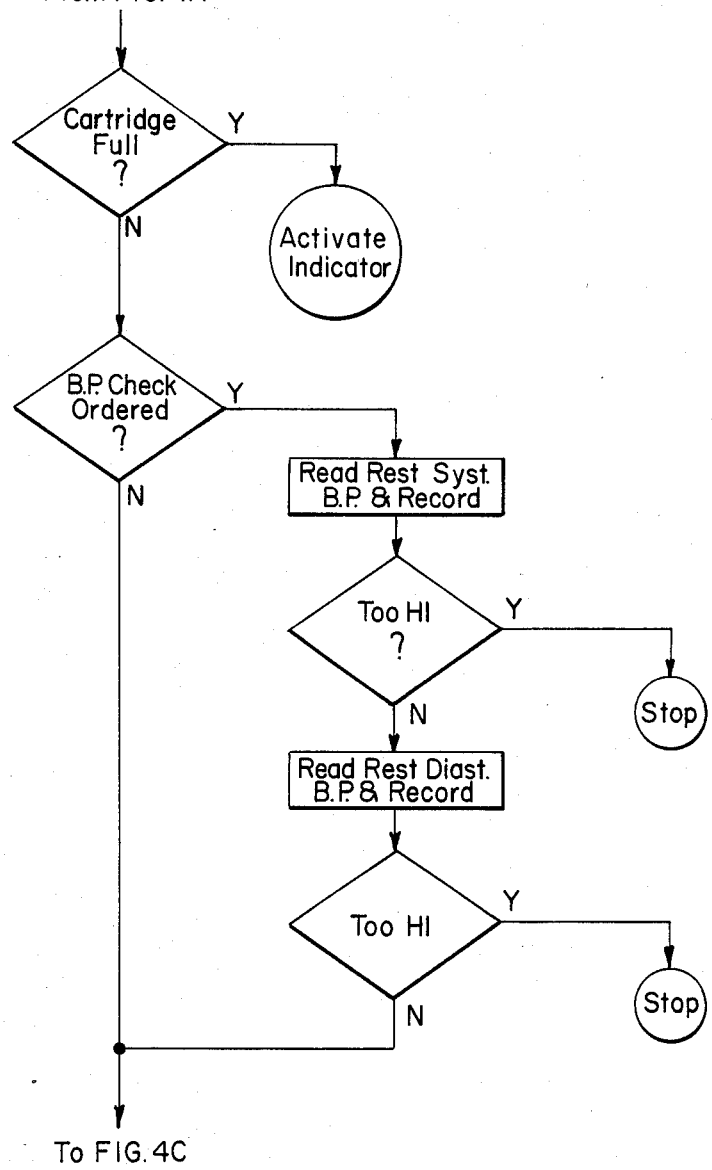
Figure 4C:
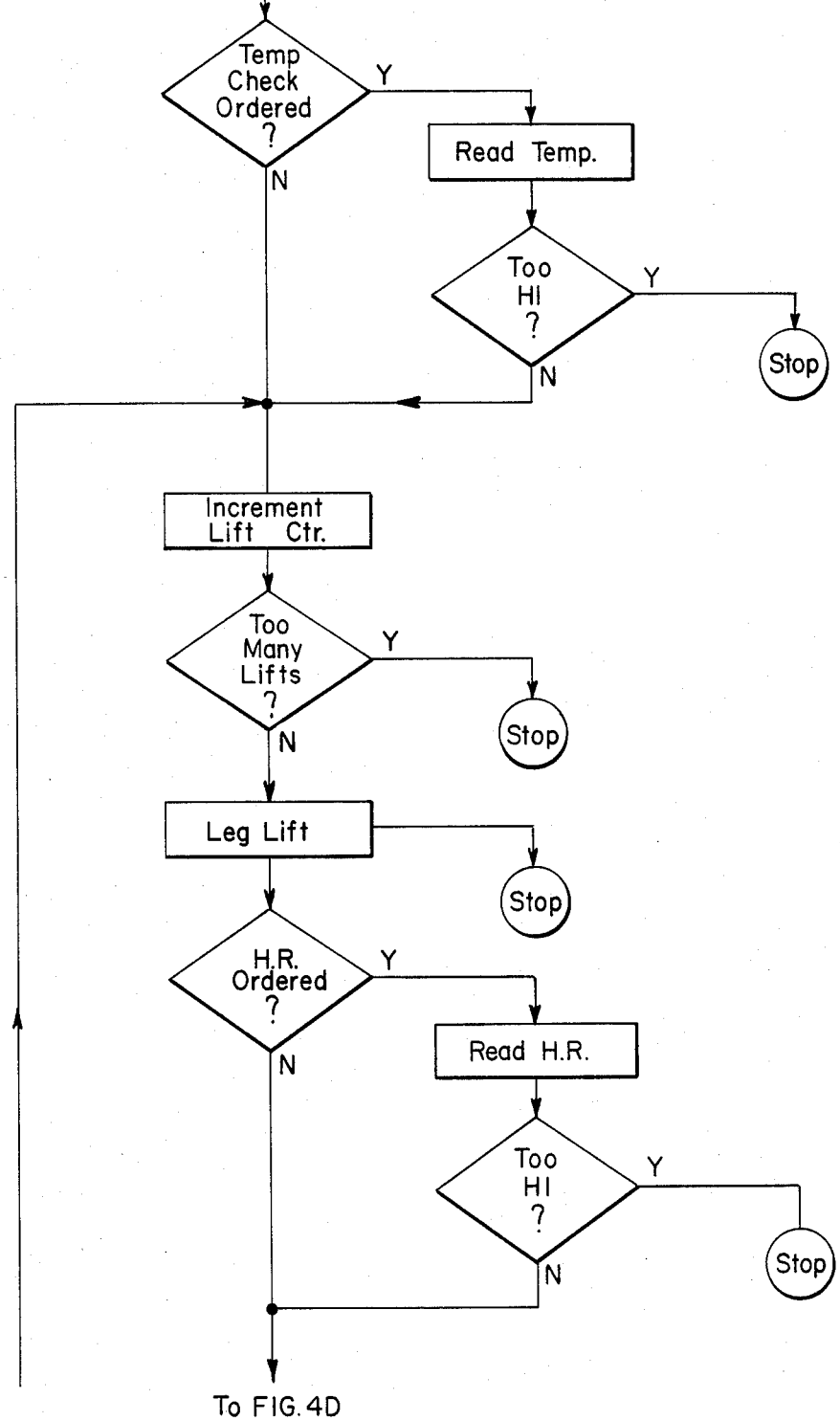
Figure 4D:
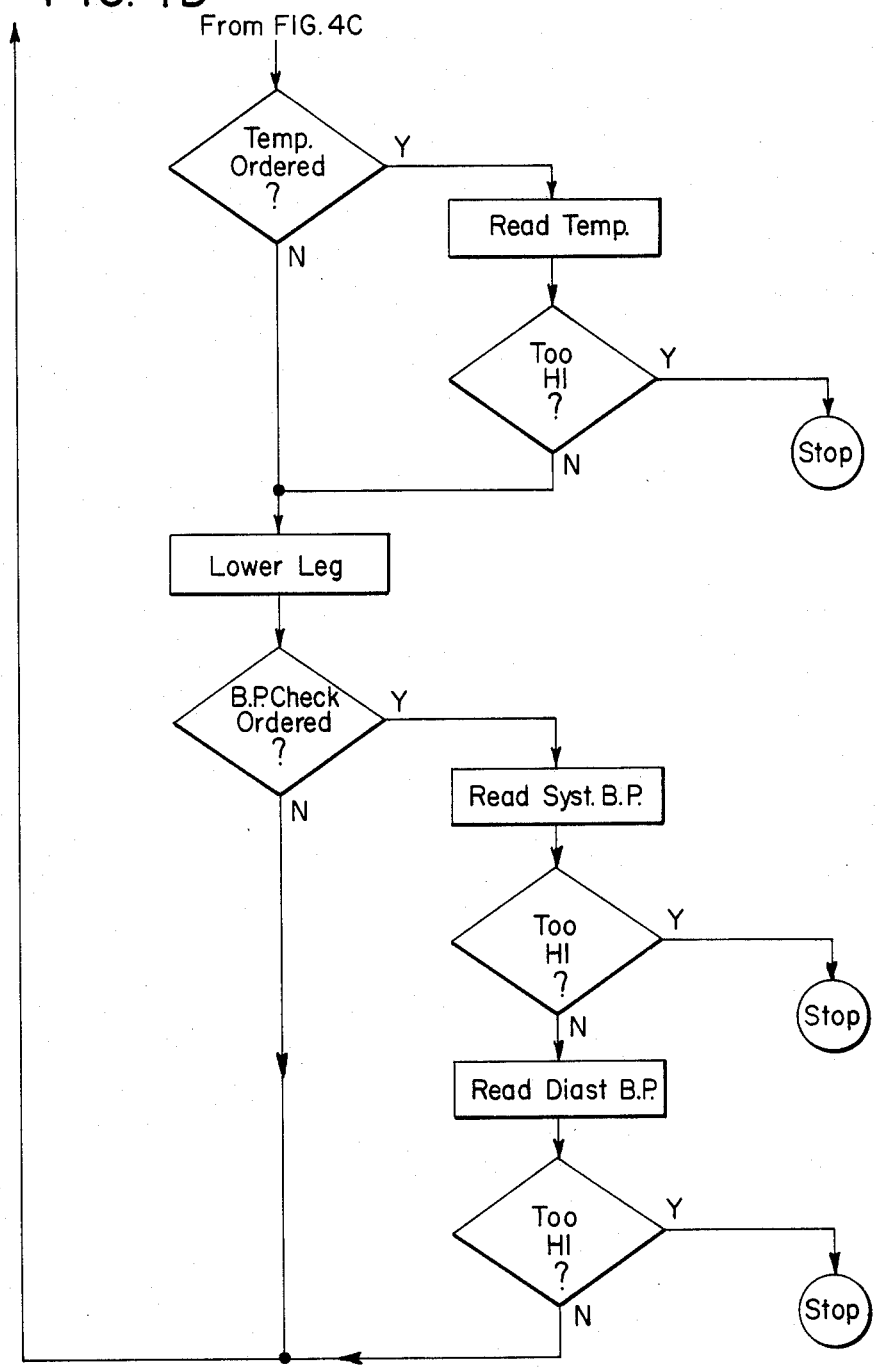

Computer 56, A/D converter 52, D/A converter 60, ramp generator 64 and stimulator 48 comprise a control system 54 which may be mounted within a console 70 as illustrated in FIG. 3. A receptacle for receipt of cartridge 58 is brought to the surface of console 70, as illustrated.

Console 70 includes a toggle switch 78 which is used to start the exercise program and a push button 76 which stops the program. A first LED 72 is illuminated when the program is active, and a second LED 73 is illuminated after an exercise routine has been completed. The console also has a digital display 68 and a series of switches which are available for implementing embodiments of the invention not described here in detail.

Figure 10:
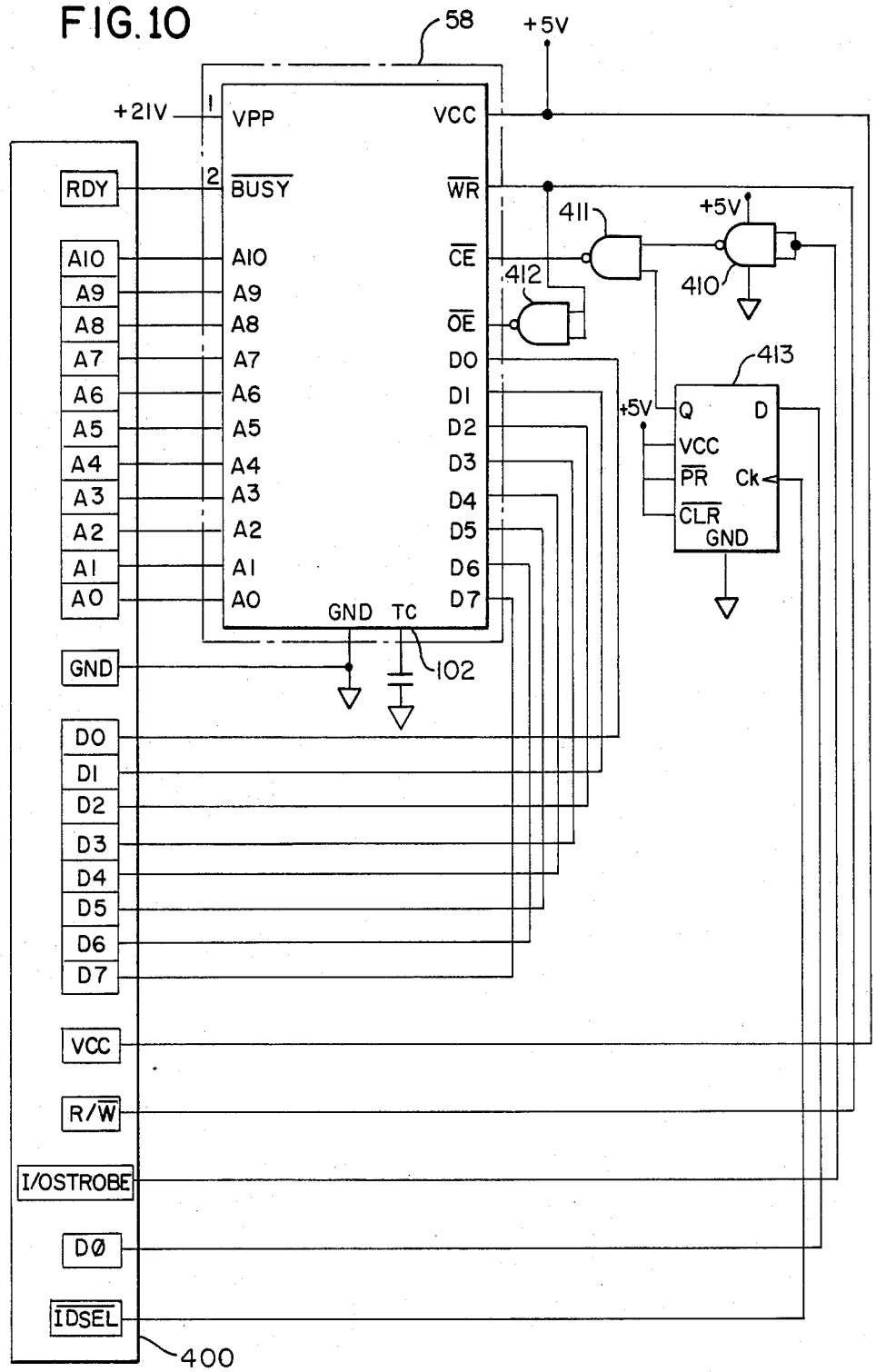
FIG. 10 is a schematic diagram of a computer connected for programming a read only memory cartridge.

The computer at the physician's programming center may be an APPLE II PLUS personal computer manufactured by Apple Computer, Inc. of Cupertino, Calif. A typical computer as illustrated by the reference numeral 400 on FIG. 10 is provided with an adapter comprising NAND gates 410 through 412 and a flip-flop 413 combined into an assembly which plugs into slot 4 of the computer. Cartridge 58 then plugs into the adapter with pin connections as shown. The pin connections are standard pin connections for the APPLE II PLUS computer and for a 2817 EEPROM (indicated by the reference numeral 102).

When cartridge 58 is taken to the exercise center and plugged into computer 56 it becomes interconnected with a microprocessor 101, as illustrated in FIG. 6A. As noted above, microprocessor 101 is a Z80 microprocessor. FIG. 6A illustrates connections for various standard Z80 terminals. Cartridge 58 (including its EEPROM 102) and microprocessor 101 are interconnected with a 6116 read/write memory 103 as also illustrated in FIG. 6A and a decoder 104 and flip-flop 105 as illustrated in FIG. 6B. Decoder 104 may be a 74LS138 integrated circuit and flip-flop 105 may be a 74LS73 integrated circuit. FIG. 6B also illustrates a crystal oscillator 108 which may operate at a frequency of 2 MHz for use as a system clock.

Computer 56 also includes a Z80 parallel input/output port 113 interconnected to microprocessor 101 as illustrated in FIG. 7. Interconnections between FIG. 7 and FIG. 6A are shown by corresponding reference numerals on lead lines.

In the preferred embodiment exercise control system 54 includes six D/A converters 60 and six stimulators 48, so that the system may be used for stimulated exercise on an exercycle or an exercise chair. One such D/A converter and stimulator are illustrated in FIG. 8. D/A converters 60 may be a DAC0832 integrated circuit. Stimulator 48 comprises integrated circuits 301 through 303, and transistors 304 through 310 connected as illustrated in FIG. 8 and operating as described in detail in Ser. No. 417,935. Stimulator 48 generates pairs of alternately pulsed signals which are applied to electrodes 46A through 46C to stimulate muscular activity in the leg of the patient.

A/D converter 52 may be an ADC0808 integrated circuit connected as illustrated in detail in FIGS. 9A and 9B. Ramp generator 64 includes an integrated circuit 357 and other components as described in detail in Ser. No. 417,935. Ramp generator 64 supplies a triangular wave to input terminal No. 5 of A/D 52.

Load cell 38 includes a strain gage 371 incorporated into a bridge network as illustrated in FIG. 9B. Output signals from the bridge network are amplified by operational amplifiers 365 and 359 and applied to input terminal 0 of A/D converter 52. Temperature sensor 88 includes a thermister 386 connected into a bridge network in a manner similar to the connection for strain gage 371. Temperature sensing signals from temperature sensor 88 are applied to input port 1 of A/D converter 52, while heart rate signals, blood pressure sound signals and blood pressure signals are applied to input ports 2 through 4 respectively. Leg extension indicating signals from potentiometer 44 are applied to input port 6 of A/D converter 52. The output lines from A/D converter 52 are marked on FIG. 9A with reference numerals indicating interconnections with circuitry illustrated on FIGS. 6A and 6B.

As illustrated in FIG. 9B electrosphygmomometer 86 has two input lines 405 and 394. Line 405 carries a sound signal while line 394 carries a pressure signal. The pressure signal is an analog voltage whereas the sound signal is an AC voltage that varies with Korotkoff sounds issued by the artery of the patient during the release of pressure within an inflatable cuff surrounding the patient's arm. The sound signal is converted to a DC voltage by an RMS converter comprising an operational amplifier 402, a diode 403, a resistor 407 and a compacitor 401. The computer system is programmed to determine the systolic blood pressure and the diastolic blood pressure by recording the pressure indicated at input terminal 4 of A/D converter 52 during predetermined values of the sound signal appearing at input port 3.

A suitable program for controlling the physician's computer during storage of exercise control parameters on cartridge 58 is set forth in TABLE I hereto. TABLE II sets forth a listing for a program to control computer 56 in response to data so stored on cartridge 58. The program set forth in TABLE I is written in a version of BASIC suitable for interpretation by a CP/M operating system. The program is stored on a disk for loading into computer 400 prior to cartridge programming. FIGS. 11A through 11D present a flow chart for that program.

The program, as outlined in the flow chart of FIGS. 11A through 11D is generalized for enabling writing data on the cartridge and reading data from the cartridge. Furthermore, the program can be used for setting up a cartridge to control either pedaling on an exercycle or leg lifting as described in the example disclosed herein. The following discussion will be limited to those aspects of the program dealing with leg lifting.

After the program has been loaded into the computer, the physician is directed to enter an input which will select either the cartridge programming routine or the cartridge reading routine. If the programming routine is selected, then the physician is directed to select options indicating those physiological parameters which are to be monitored during the exercise phase. Selection options include heart rate, blood pressure and temperature. The option selections are used later in the program for controlling the input of limits for the selected physiological parameters. The option selections are also used to set the value for a variable stored in hexidecimal location 960F. At a later point the program reads that memory location and burns a corresponding value into cartridge location 060F. In carrying out such storage and retrieval the program utilizes a reference number referred to as "BASE" which has a value of 9000 Hex. This is necessary because the computer utilizes storage location 060F for other purposes and cannot make that location available for temporary storage of exercise control parameters. All other temporary storage for cartridge support is likewise shifted in memory by using the reference number BASE.

Selection of heart rate, blood pressure and temperature options is accomplished by selecting one of the letters Y or N for each of the variables H$, B$ and T$. After this selection has been made, the computer instructs the physician to select an exercise level. In the case of a leg lifting exercise the selected number represents the number of leg lifts being prescribed.

Following selection of the exercise level the physician selects the maximum permitted heart rate, both at rest and during exercise. Then selections are made for maximum permitted values for systolic blood pressure and diastolic blood pressure (rest values and exercise values for each) and maximum permitted body temperature (at rest and during exercise). All values for the above-noted physiological limits are stored in memory at locations shifted above the corresponding cartridge locations by the amount BASE.

The next step in the program is the selection of the type of exercise. For the program listed in TABLE I leg lifting is selected by inputing the letter "A" as the value for a variable called A$. During this same part of the program the physician prescribes the maximum number of cartridge uses, and the computer sets an appropriate corresponding number into the use counter. The program will accept any prescribed number of uses up to a maximum of 16. At this point the program also calculates a number for insertion into location 960F Hex. for indicaton of the physiological parameters which are to be monitored.

If the physician has selected leg lifting as the prescribed exercise, then the computer next instructs selection of a code designating the muscle group to be exercised, a number indicating the weight of the load to be lifted, and a number identifying the patient. It should be noted at this point that the muscle designation code is used only for read out to the physician after the cartridge has been returned. The accompanying written prescription must designate the muscle type for use by operators at the exercise center.

The last step in the cartridge programming routine is the burning of the EEPROM for storage of all exercise control data. As noted above, the cartridge storage locations differ from corresponding storage locations in computer 400 by the value BASE.

Figure 11A:
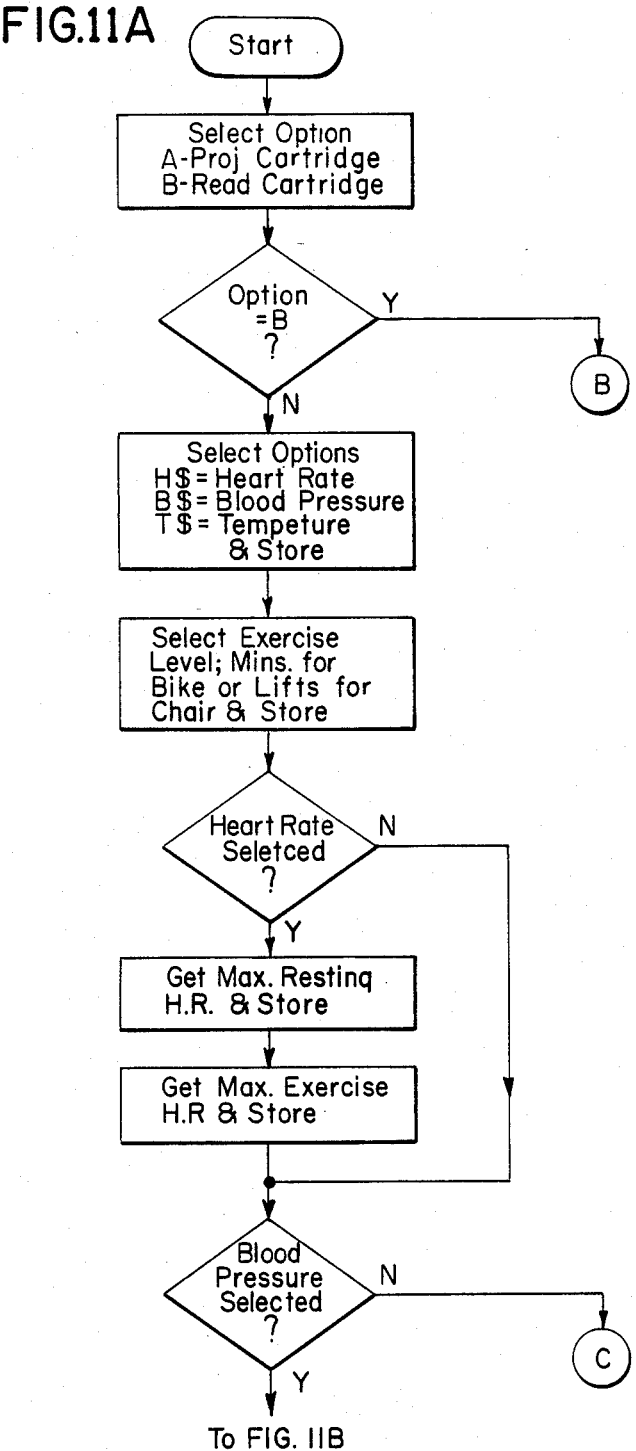
FIGS. 11A-11D are a flow chart for a computer program to store exercise control data in a memory cartridge.
Figure 11B:
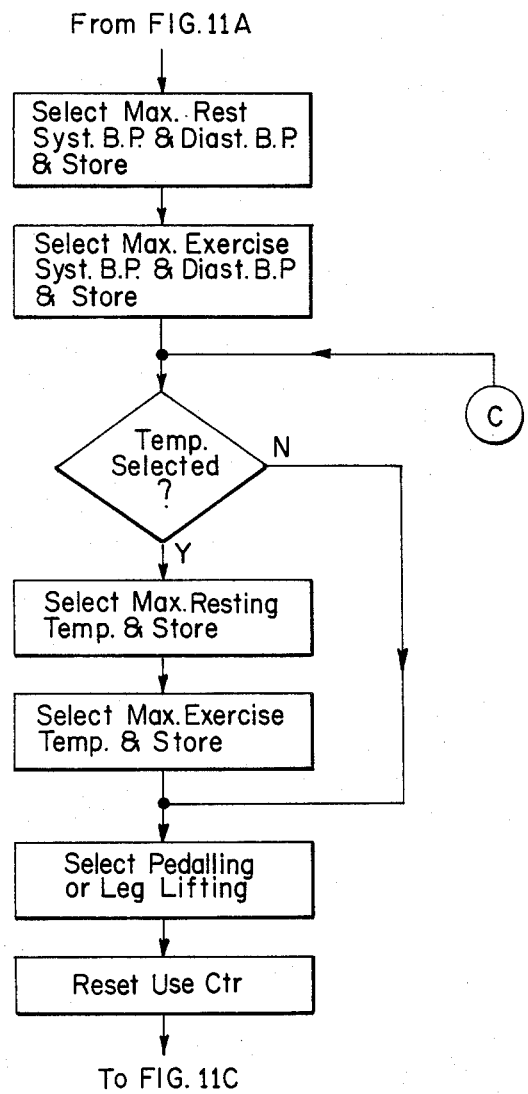
Figure 11C:
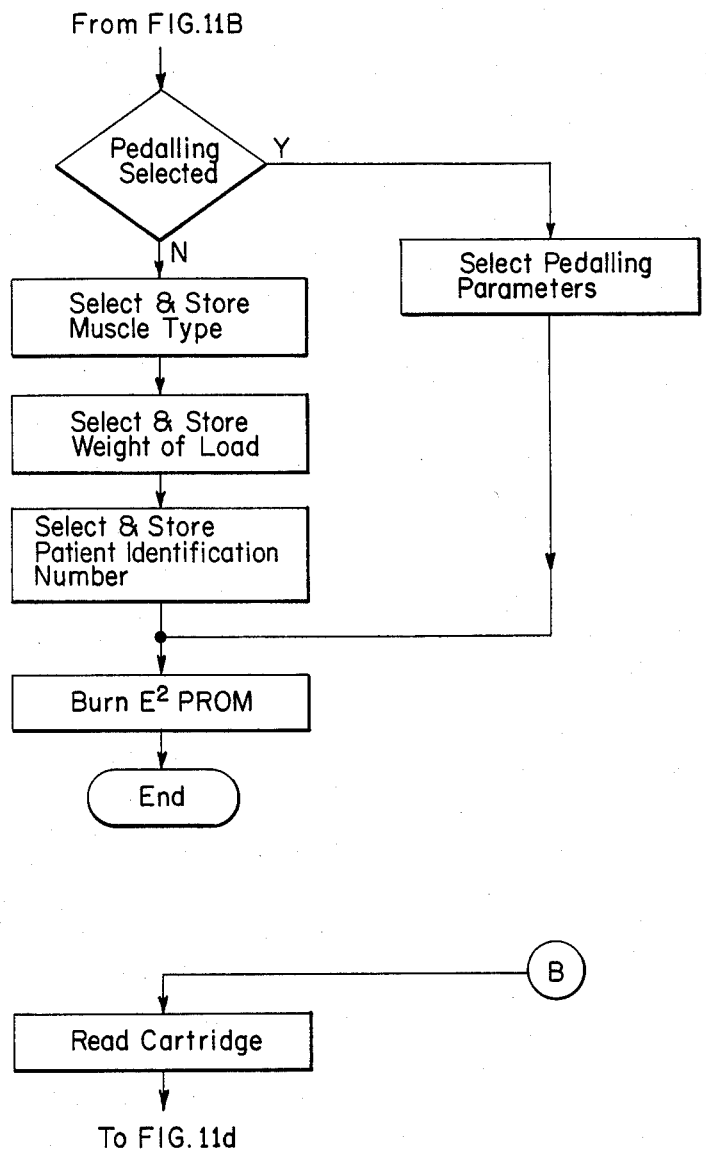
Figure 11D:
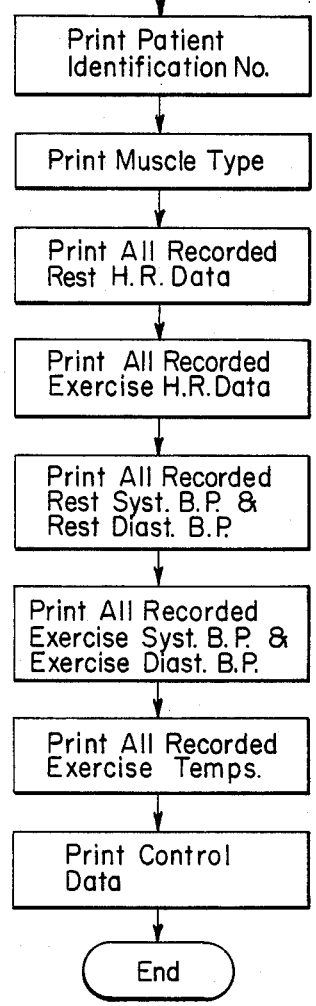

If the physician has selected the cartridge read option, then the computer proceeds to read out the cartridge data in the sequence generally illustrated in FIG. 11D. The data so read out includes the limits reached by the designated physiological parameters during each exercise session, together with the number of leg lifts achieved each time. The data so read out is placed in memory within the computer beginning at storage location 9000 Hex. All recorded data is also printed out for use by the physician in prescribing further treatment.

FIGS. 4A through 4D and FIG. 5 illustrate the logical operations carried out by the exercise system in response to the data stored in cartridge 58. As noted in FIG. 4A the first step is to read the load being supported by the load cell 38. This is done before any leg stimulation has been commenced, as a check of the system set up. This is accomplished by calling a weight routine which strobes A/D converter 52 and thereafter reads the data and the memory location assigned to data from load cell 38. The data so read is compared against the weight limits stored in cartridge 58. If the measured weight exceeds the weight limit, then the program branches to a stop routine.

The stop routine is not illustrated in detail in FIGS. 4A through 4D. This routine may be entered from a number of different points in the program. Upon execution, this routine proceeds to store leg the lift count, systolic blood pressure, diastolic blood pressure, heart rate and body temperature in cartridge 58. The stop routine also increments the cartridge use count and stores the incremented count into cartridge 58.

After the load weight has been checked, the system makes an inquiry to determine whether or not a heart rate check has been ordered. If so, then the heart rate is read and recorded and checked against the maximum prescribed resting heart rate. Again, the stop routine is entered if the limit is exceeded.

Following the heart rate check the system checks to determine whether or not the cartridge usage limit has been reached. If so, the system activates an indicator on control console 70 and proceeds no further.

If the cartridge usage limit has not been reached, then the system checks to determine whether or not blood pressure recording has been ordered. If so, the systolic and diastolic blood pressures are read and compared against prescribed resting limits. Systolic blood pressure readings are made by pressurizing a cuff which surrounds the arm of the patient and which forms a part of blood pressure sensor 86. The pressure on the cuff is released, and the computer observes the readings received at input port 3 of A/D converter 52. As noted above, these are converted sound reading from the sound channel of sensor 86. When the sound reading has a value of 50 Hex., then the pressure reading appearing at input port 4 of A/D converter 52 is read and recorded as the systolic blood pressure. The system determines the diastolic blood pressure by reading the pressure at input port 4 of A/D converter 52 when the sound reading at input port 3 has a value of 20 Hex.

Following the blood pressure check, the system performs a temperature check, if ordered, and compares the observed temperature against the prescribed temperature limit.

After the initial checking of the weight and the prescribed physiological parameters has been completed, the program enters its leg lifting routine. That routine commences by incrementing a lift counter and comparing the count in that counter against the maximum prescribed number of leg lifts. If the maximum count is exceeded (which, of course ordinarily will not occur during the first pass through the loop), then leg stimulation commences. During the stimulation phase the system observes the signal from the ramp generator 64 and compares it against the leg position signal received from potentiometer 44. Stimulation commands are applied to D/A converter 60 and stimulator 48 as appropriate to cause the feedback signal to track the ramp signal. This is all indicated by a single block on FIG. 4C. The details of the leg lifting control logic are set forth in FIG. 5. As noted in that figure, the STOP routine is entered if the stimulation voltage exceeds a maximum value of 250 volts. The STOP routine is also entered if the knee becomes hyperextended.

Figure 5:
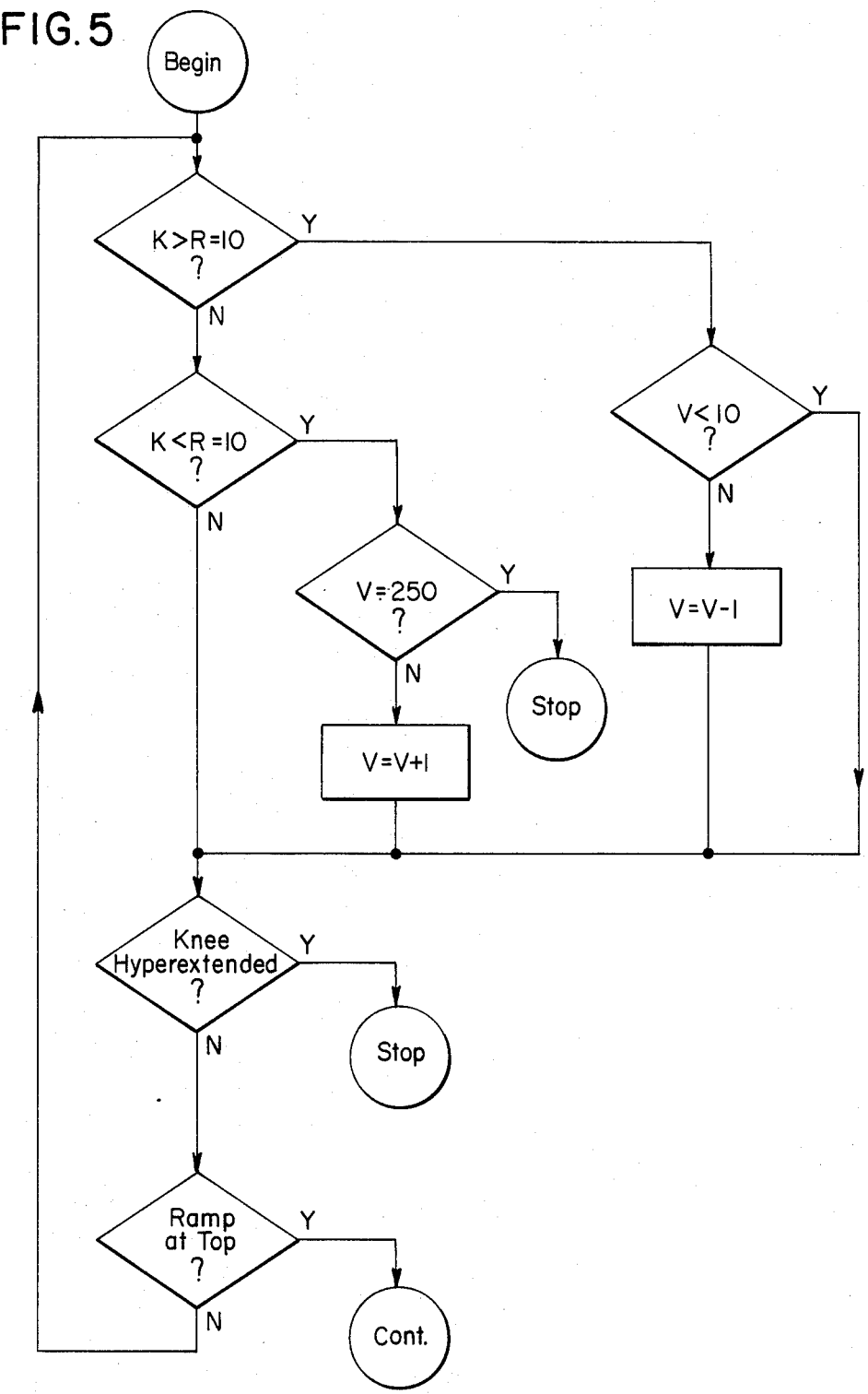
FIG. 5 is a flow chart for a computer routine to control leg lifting.

The stimulation command which is generated for stimulator 48 by D/A converter 60 is latched to a constant value and is periodically modified by computer 56. As illustrated in FIG. 5 the stimulation voltage is increased by one unit, if a maximum value of 250 has not been reached and if the knee angle is more than ten units smaller than any ramp angle. The stimulation voltage is decreased by one unit if it has a value greater than ten and if, further, the knee angle is more than ten units greater than the ramp angle.

The system determines that the knee has become hyperextended whenever the knee angle measurement exceeds 127 units, thereby raising the computer's negative status flag. This causes entry into the stop routine as stated above. So long as the knee does not become hyperextended, the stimulation is continued in such a manner as to cause the knee angle to track the ramp angle. The maximum ramp angle is 120 units, as established by the design of ramp generator 64. The computer continually monitors the ramp angle, and when this angle reaches a value of 120 units, then an exit is made from the stimulation routine, and the logic of FIG. 4C continues.

The continuing logic involves heart rate reading and temperature reading, as prescribed, and comparison of these readings against prescribed limits. This reading and limit comparison is followed by a leg lowering routine which is not illustrated in detail, but which is similar to the routine of FIG. 5. Following the leg lowering routine the system checks the systolic and diastolic blood pressures and compares them against prescribed limits, as appropriate. Thereafter, the system again increments the lift counter and proceeds with another lifting cycle.

It will be appreciated that the exercise system 10 produced by the invention herein described is not limited to the use of transcutaneous stimulators, nor is it applicable only to the lower limbs of a human subject. It is believed that comparable devices for exercising neck muscles, arm muscles and stomach muscles, all using stimulators and a strap and pulley arrangement similar to that shown in FIG. 1, may be developed and fall within the scope of the invention. Furthermore, the invention is not confined to systems using closed loop feedback control but may be applied to open loop systems as well.

While the method herein described and the form of apparatus for carrying this method into effect constitute preferred embodiments of this method, it is to be understood that the invention is not limited to this precise form of apparatus and that changes may be made in either without departing from the scope of the invention.

TABLE I

```
]        LIST

1        REM    ************************
2        REM    CARTRIDGE SYSTEM PROGRAMMER*
3        REM    ************************
4        REM
```

```
5          REM   COPYRIGHT WRIGHT STATE UNIVERSITY 1984
6          REM
7          REM   ASSUME PROGRAM ON CARTRIDGE MUST BE 2K OR
LESS
8          REM   RESERVED MEMORY IS IN EEPROM IN LAST BLOCK
9          REM   START AT 0600H FOR RESERVED AREA
10         REM   USE 0600=SUBJECT ID
11         REM   USE 0601=DATE
12         REM   USE 0602=WORK TYPE..LOWER 4 BITS=WEIGHT
LIFT..
                 UPPER=BIKE WITH FORMAT BELOW
13         REM   01H=QUAD
EXERCISE..02H=HAMSTRING...03H=GASTROC
                 ...04H=TIBIAL...05H=TRICEPS...06H=BICEPS
14         REM
15         REM   10H=BIKE QUAD AND GLUT ONLY
16         REM   20H=BIKE QUAD, GLUT, HAM
17         REM   30H=BIKE QUAD, GLUT, HAM ILIACUS
20         REM
21         REM
22         REM   06F0=HR MAX REST, 06F1=BP MAX SY REST,
                 06F2=MAX DIA REST, 06F3=TEMP MAX REST,
                 06F4=HR MAX EXERCISE, 06F5=SYST MAX EX
23         REM   06F7=DIA MAX EX, 06F8=TEMP MAX EX,
                 06FE=WORKLOAD IN KP OR LBS
24         REM   06FF=LOAD LIMIT IN 1/16 KP OR LBS
25         REM
26         REM   0700-07FF=DATA FROM RUNS AS EITHER NUMBER
                 OF BIKE ROTATIONS OR NUMBER OF LIFTS
27         REM
28         REM   0700-070F=RUNS
29         REM   0720-072F=REST HR
30         REM   0710-071F=EX HR
31         REM   0730-073F=REST SYS
32         REM   0740-074F=REST DIA
33         REM   0750-075F=EX SYST
34         REM   0760-076F=EX DIA
35         REM   ***06F6=USE COUNTER MAX=15
50         BASE = 9000H
51         REM   CARTRIDGE MUST BE IN SLOT 4
52         REM   *************************
53         REM
100        FOR I = 1 TO 30: PRINT : NEXT I
110        PRINT "CARTRIDGE CONTROL PROGRAM"
120        PRINT
130        PRINT "SELECT OPTION BY TYPING LETTER"
140        PRINT
150        PRINT "      A) PROGRAM MASTER"
160        PRINT :     B) READ CARTRIDGE"
165        FOR I = 1 TO 10: PRINT : NEXT I
170        INPUT A$
180        IF A$ = "A" THEN GO TO 1000
190        IF A$ = "B" THEN GO TO 9000
200        PRINT "INPUT ERROR...TRY AGAIN": GO TO 170
1000       REM   START PROGRAM MASTER
1010       REM   BINARY PROGRAM MUST BE STORED IN HIGH
                 MEM AT 9000H=BASE
```

```
1020      REM  SUBROUTINE FOR PROGRAMMING MASTER
1030      FOR I = 1 to 30: PRINT : NEXT I
1040      PRINT "PROGRAM MASTER CARTRIDGE"
1050      PRINT : PRINT : PRINT "DO YOU WANT HEART
RATE?(Y/N)
1060      INPUT H$
1070      PRINT "DO YOU WANT BP(Y/N)" : INPUT B$
1080      PRINT "DO YOU WANT TEMP(Y/N)": INPUT T$
1081      PRINT "HOW MUCH EXERCISE DO YOU WANT?
1082      PRINT : PRINT " ENTER IN MINS FOR BIKE
              OR NO OF LIFTS FOR CHAIR"
1083      INPUT X
1084      IF X > 255 THEN GO TO 1083
1085      FOR I = 0700H TO 070FH
1086      POKE BASE + I,X
1087      NEXT I
1089      PRINT : PRINT
1100      IF H$ = "N" THEN GO TO 1500
1110      IF H$ = "Y" THEN GO TO 1120 : GO TO 2000
1120      PRINT : PRINT : PRINT
1130      PRINT "WHAT IS MAX RESTING HR"
1140      INPUT M
1150      POKE BASE + 0650H,M
1160      PRINT "WHAT IS MAX EXER. HR"
1170      INPUT M
1180      POKE BASE + 06F4H,M
1500      IF B$ = "Y" THEN GO TO 2500
1600      IF T$ = "Y" THEN GO TO 3000
1700      GO TO 3500
2000      GO TO 1500
2499      GO TO 1500
2500      REM  SET UP BLOOD MAX
2510      FOR I = 1 TO 30: PRINT : NEXT I
2520      PRINT "WHAT IS THE MAX SYST./DIA BP AT REST?"
2530      PRINT : PRINT "INPUT SYST AND DIA"
2540      FOR I = 1 TO 5: PRINT : NEXT I
2550      INPUT S,D
2555      IF S OR D > 255 THEN GO TO 2557
2556      GO TO 2560
2557      PRINT "ERROR ON LIMIT...TRY AGAIN": GO TO 2550
2560      POKE BASE + 06F1H,S: POKE BASE + 06F2H,D
2570      FOR I = 1 TO 5: PRINT : NEXT I
2580      PRINT "WHAT ARE THE MAXIMUM SYST AND DIA BP?"
2590      FOR I = 1 TO 5: PRINT : NEXT I
2600      INPUT S,D
2610      IF S OR D   255 THEN GO TO 2615
2612      GO TO 2620
2615      PRINT "INPUT RANGE ERROR..TRY AGAIN": GO TO 2600
2620      POKE BASE + 06F5,S
2630      POKE BASE + 06F7,D
2999      GO TO 1600
3000      REM  SET UP TEMP MAX
3010      FOR I = 1 TO 30: PRINT : NEXT I
3019      PRINT "TEMP IN DEG C ONLY"
3020      PRINT "WHAT IS THE MAX RESTING TEMP?": INPUT T
3030      IF T > 20 OR T < 45 THEN GO TO 3050
```

```
3040    PRINT "RANGE ERROR..TRY AGAIN": GO TO 3020
3050    POKE BASE + 06F3H,T
3060    FOR I = 1 TO 30: PRINT : NEXT I
3070    PRINT "INPUT MAX TEMP IN DEG C EXERCISE?": INPUT T
3080    IF T > 20 OR T < 45 THEN GO TO 3100
3090    PRINT "RANGE ERROR .. RETYPE FOR SAFER TEMP":
            GO TO 3070
3100    POKE BASE + 06F8H,T
3499    GO TO 3500
3500    REM  PROGRAM TYPE OF EXERCISE
3510    REM  SET REGISTERS FOR LIMITS
3520    IF H$ = "N" THEN POKE BASE + 06F0H,255
3521    REM  SET USE COUNTER
3522    PRINT
3523    PRINT "HOW MANY CARTRIDGE USES"
3524    INPUT USE
3525    IF USE = 0 then GOTO 3524: PRINT
3526    IF USE > 16 THEN GOTO 3523
3527    USE = 16 - USE
3528    POKE BASE + 06F6H,USE
3530    REM  SET TEST CONTROL
3540    TEST = 0
3550    IF H$ = "Y" THEN TEST = TEST + 1
3560    IF B$ = "Y" THEN TEST = TEST + 2
3570    IF T$ = "Y" THEN TEST = TEST + 4
3580    POKE BASE + 060FH, TEST
3590    REM
3600    FOR I = 1 TO 30: PRINT : NEXT I
3610    PRINT "WHAT TYPE OF EXERCISE"
3620    PRINT "       A) BIKE"
3630    PRINT "       B) WEIGHTS"
3635    FOR I = 1 TO 5: PRINT : NEXT I
3640    INPUT A$
3650    IF A$ = "B" THEN GOTO 4000
3670    IF A$ = "A" THEN GOTO 5000
3700    PRINT "INPUT ERROR TRY AGAIN": GOTO 3610
4000    REM  WEIGHTS SET
4010    FOR I = 1 TO 30: PRINT : NEXT I
4020    PRINT "SELECT MUSCLE TO BE USED"
4030    PRINT "       A) QUAD"
4040    PRINT "       B) HAMSTRING"
4050    PRINT "       C) GASTROC"
4060    PRINT "       D) TIBIAL"
4070    PRINT "       E) TRICEPS"
4080    PRINT "       F) BICEPS
4100    INPUT A$
4110    IF A$ = "A" THEN POKE 0602H + BASE,01
4120    IF A$ = "B" THEN POKE BASE + 0602H,02
4121    WERK = BASE + 0602H
4130    IF A$ = "C" THEN POKE WERK,03
4140    IF A$ = "D" THEN POKE WERK,04
4150    IF A$ = "E" THEN POKE WERK,05
4160    IF A$ = "F" THEN POKE WERK,06
4170    REM  MUSCLE IS NOW SET UP
4180    FOR I = 1 TO 5: PRINT : NEXT I
4190    PRINT "WHAT IS THE MAXIMUM WORK LOAD"
```

```
4195        PRINT "DO NOT EXCEED 30 LBS"
4200        PRINT
4210        INPUT W
4215        IF W   30 THEN GOTO 4210
4220        POKE BASE + 06FFH,W
4230        FOR I = 1 TO 5: PRINT : NEXT I
4240        PRINT "WHAT IS THE SUGGESTED LOAD"
4250        PRINT
4260        PRINT "MUST BE LESS THAN 30 LBS"
4270        INPUT W
4280        IF W > 30 THEN GOTO 4260
4290        POKE BASE + 06FEH,W
4300        GOTO 8000
4999        GOTO 7000
5000        REM   BIKE SET
5010        FOR I = 1 TO 30: PRINT : NEXT I
5015        PRINT "BIKE CONTROL": PRINT
5020        PRINT "WHAT MUSCLE COMBINATION DO YOU WANT?"
5030        PRINT "        A) QUAD AND GLUT ONLY"
5040        PRINT "        B) QUAD, GLUT, HAM
5050        PRINT "        C) QUAD, GLUT, HAM, IL"
5060        PRINT
5070        INPUT A$
5075        WERK = BASE + 0602H
5080        IF A$ = "A" THEN POKE WERK,10H
5090        IF A$ = "B" THEN POKE WERK,20H
5100        IF A$ = "C" THEN POKE WERK,30H
5200        PRINT : PRINT : PRINT "WHAT IS LOAD MAX"
5210        PRINT "MAX <1 KP  IN 1/16 KP INCRE"
5220        INPUT W
5230        IF W >16 OR  < 0 THEN GOTO 5210
5240        POKE BASE + 06FFH,W
5250        PRINT : PRINT : PRINT "WHAT IS WORKLOAD?"
5260        PRINT "RANGE 1 TO 16 IN 1/16 KP"
5270        INPUT W
5280        IF W >16 or < 0 THEN GOTO 5260
5290        POKE BASE + 06FEH,W
5300        GO TO 8000
5999        GO TO 7000
7000        REM   SUBJECT ID AND BURN
7010        FOR I = 1 TO 30: PRINT : NEXT I
7020        PRINT "WHAT IS THE SUBJECT ID?"
7030        PRINT "RANGE= 1 TO 255"
7040        INPUT S
7050        POKE BASE + 0600H,S
7060        FOR I = 1 TO 30: PRINT : NEXT I
7070        PRINT "EEPROM IS BURING IN NOW"
7074        REM   BURN=LOC OF EEPROM
7075        BURN = C800H
7076        REM   ACTIVATE BURN:POKE 50176,1
7080        FOR I = BASE TO BASE + 2000H
7090        POKE BURN, PEEK (I)
7100        FOR X = 1 TO 5: NEXT X
7105        BURN = BURN + 1
7110        NEXT I
7115        POKE 50176,0
```

```
7200        PRINT "PROM IS SET..PROGRAM OVER"
7210        END
8000        REM  SUBJECT ID
8010        FOR I = 1 TO 30
8020        PRINT
8030        NEXT I
8040        PRINT "WHAT IS THE SUBJECT ID NO"
8050        PRINT "MUST BE 1-255"
8060        INPUT W
8070        IF W > 255 THEN GOTO 8050
8080        IF W < 0 THEN GOTO 8050
8090        POKE BASE + 0600H,W
8100        PRINT
8110        GOTO 7000
9000        REM  CARTRIDGE PRINT OUT
9010        FOR I = 1 to 30
9020        PRINT
9030        NEXT I
9031        REM  *****READ CART TO 9000H HERE**
9032        GOTO 10000
9040        PRINT "CARTRIDGE PRINTOUT"
9050        PRINT : PRINT "PRINTER ON"
9060        PR# 1
9080        PRINT "SUBJECT ID": PRINT PEEK (BASE + 0600H)
9090        W = PEEK (BASE + 0602H)
9100        IF W > 16 THEN PRINT "BIKE WORK"
9110        IF W < 16 THEN PRINT "WEIGHT WORK"
9120        IF W = 16 THEN PRINT "WEIGHT WORK"
9130        PRINT : PRINT : PRINT
9140        PRINT "MUSCLE USE"
9150        IF W = 1 THEN PRINT "QUAD"
9160        IF W = 2 THEN PRINT "HAMSTRING"
9170        IF W = 3 THEN PRINT "GASTROC"
9180        IF W = 4 THEN PRINT "TIBIAL"
9190        IF W = 5 THEN PRINT "TRICEPS"
9200        IF W = 6 THEN PRINT "BICEPS"
9210        IF W = 10H THEN PRINT "QUAD AND GLUT"
9220        IF W = 20H THEN PRINT "QUAD, GLUT,HAM"
9230        IF W = 30H THEN PRINT "QUAD,GLUT,HAM,ILIAC"
9240        PRINT : PRINT : PRINT
9250        PRINT "PRINT DATA"
9260        PRINT "RUNS DATA"
9265        WERK = PEEK (BASE + 06F6H)
9270        FOR I = 1 TO WERK
9280        PRINT I, PEEK (I + BASE + 06FFH)
9290        NEXT I
9300        PRINT : PRINT : PRINT : PRINT
9310        PRINT "REST HR DATA"
9320        FOR I = 1 TO WERK
9330        PRINT I, PEEK (I + BASE + 071FH)
9340        NEXT I
9350        PRINT : PRINT : PRINT : PRINT "EX HR"
9360        FOR I = 1 TO WERK: PRINT I, PEEK (I + BASE +
070FH): NEXT I
9370        PRINT : PRINT : PRINT "REST SYST AND DIA"
9390        FOR I = 1 TO WERK
```

```
9400        PRINT I, PEEK (BASE + I + 072FH), PEEK (BASE + I
+ 073FH)
9410        NEXT I
9420        PRINT : PRINT : PRINT "EX SYST AND DIA"
9430        PRINT
9440        FOR I = 1 TO WERK
9450        PRINT I, PEEK (BASE + I + 074FH), PEEK (BASE + I
+ 075FH)
9460        NEXT I
9470        PRINT : PRINT : PRINT : PRINT "TEMP DATA"
9480        FOR I = 1 TO WERK
9490        PRINT I, PEEK (BASE + I + 076FH)
9500        NEXT I
9510        PRINT "CONTROL DATA"
9520        FOR I = 96F0H TO 96FFH
9530        PRINT PEEK (I): NEXT I
9540        PRINT : PRINT "END"
9550        PR# 0
9560        END
10000       REM  CARTRIDGE READ TO 9000H
10010       REM  SET CARTRIDGE TO READ
10020       POKE 50176,0
10030       FOR I = 1 TO 2000
10040       POKE 9000H + (I - 1), PEEK (C800H - 1 + I)
10050       NEXT I
10999       GOTO 9040
]
```

TABLE II

```
 1:                    ; PARALLEL OUT FOR LIGHTS     IN FOR SWITCH
 2:
 3:
 4:
 5:                    ; AD5=RAMP     AD6=LEG POSITION
 6:
 7:                    ; COPYRIGHT   WRIGHT STATE UNIVERSITY   1984
 8:
 9:
10:
11:  0000              ORG 0000H
12:
13:                    ;         MAIN PROGRAM
14:
15:
16:  0000  3E00        MVI A,00
17:  0002  320040      STA 4000H
18:  0005  320140      STA 4001H
19:  0008  320240      STA 4002H
20:  000B  320340      STA 4003H
21:  000E  320440      STA 4004H
22:  0011  320540      STA 4005H
23:  0014  D380        OUT DA
24:  0016  320640      STA 4006H
25:  0019  320740      STA 4007H
26:  001C  320840      STA 4008H
27:  001F  320940      STA 4009H
```

```
28:  0022 320A40      STA 400AH
29:  0025 320B40      STA 400BH
30:  0028 320C40      STA 400CH
31:  002B 320D40      STA 400DH
32:  002E 320E40      STA 400EH
33:  0031 320F40      STA 400FH
34:  0034 3E0F        MVI A,0FH;SET PIA FOR I/O CONFIGURATION
35:  0036 D3F1        OUT 0F1H
36:  0038 3E1F        MVI A,1FH
37:  003A D3F3        OUT 0F3H
38:  003C 3AF006      LDA 06F0H;HR HREST
39:  003F 320440      STA STORE1
40:  0042 3E00        MVI A,00
41:  0044 D380        Z3 OUT PORT
42:  0046 DBF0        IN PORT1
43:  0048 E601        ANI 01;BIT 0 GOES TO ZERO TO START
44:  004A F24400      JP Z3
45:  004D 3AFF06      LDA 06FFH
46:  0050 320440      STA STORE1
47:                   ; CHECK FOR RESTING WEIGHT TOO HIGH
48:  0053 CDA702      CALL WEIGHT
49:  0056 3E01        MVI A,01
50:  0058 D380        OUT PORT; SET VISUAL
51:  005A 3A0F06      LDA 060FH
52:  005D E601        ANI 01
53:  005F CA6500      JZ CS
54:  0062 CD2402      CALL HR
55:  0065 3AF606      CS LDA 06F6H
56:  0068 FE10        CPI 16
57:                   ; ***   CHECK FOR CARTRIDGE FULL***
58:  006A FA0202      JM OVER;STOP IF CARTRIDGE IS FULL
59:  006D C620        ADI 20H
60:  006F 6F          MOV L,A
61:  0070 3E07        MVI A,07H
62:  0072 67          MOV H,A
63:  0073 3A0240      LDA HER
64:  0076 77          MOV M,A
65:  0077 3AF106      LDA 06F1H
66:  007A 320440      STA STORE1
67:  007D 3AF206      LDA 06F2H
68:  0080 320540      STA STORE2
69:  0083 3A0F06      LDA 060FH
70:  0086 E602        ANI 02
71:  0088 CA8E00      JZ CS1
72:  008B CDB702      CALL BP
73:  008E 7D          CS1 MOV A,L
74:  008F C610        ADI 10H
75:  0091 6F          MOV L,A
76:  0092 3A0040      LDA SYSTOLIC
77:  0095 77          MOV M,A
78:  0096 CD0902      CALL DELAY
79:  0099 7D          MOV A,L
80:  009A C610        ADI 10H
81:  009C 6F          MOV L,A
82:  009D 3A0140      LDA DIASTOLIC
83:  00A0 77          MOV M,A
```

```
 84:   00A1 CD0902      CALL DELAY
 85:   00A4 3AF306      LDA 06F3H
 86:   00A7 320440      STA STORE1
 87:   00AA 3A0F06      LDA 060 FH
 88:   00AD E604        ANI 04
 89:   00AF CAB500      JZ TAG1
 90:   00B2 CD1102      CALL TEMP
 91:
 92:
 93:
 94:                    ; *START LEG UP LOOP HERE*
 95:   00B5 D3E5        TAG1OUT STROBE5
 96:   00B7 CD0902      CALL DELAY
 97:   00BA DBE5        IN AD5
 98:   00BC FE02        CPI 02
 99:   00BE C2B500      JNZ TAG1
100:   00C1 3A0740      LDA COUNT;UPDATE LIFT COUNTER
101:   00C4 C601        ADI 01
102:   00C6 320740      STA COUNT
103:
104:                    ; *SEE IF LIFTS ARE TOO MANY*
105:
106:   00C9 3AF607      LDA 07F6H
107:   00CC 6F          MOV L,A
108:   00CD 3E07        MVI A,07H
109:   00CF 67          MOV H,A
110:   00D0 7E          MOV A,M
111:   00D1 47          MOV B,A
112:   00D2 3A0740      LDA COUNT
113:   00D5 90          SUB B
114:   00D6 F23702      JP STOP
115:
116:
117:
118:
119:   00D9 D3E5        TAG2 OUT STROBE5;
START LIFTING KNEE UP LOOP HERE
120:   00DB CD0902      CALL DELAY
121:   00DE CD0902      CALL DELAY
122:   00E1 CD0902      CALL DELAY
123:   00E4 DBE5        IN AD5
124:   00E6 47          MOV B,A
125:   00E7 D3E6        OUT STROBE6
126:   00E9 CD0902      CALL DELAY
127:   00EC CD0902      CALL DELAY
128:   00EF CD0902      CALL DELAY
129:   00F2 DBE6        IN AD6
130:   00F4 90          SUB B;POSITION-RAMP
131:   00F5 FE0A        CPI 10
132:   00F7 F20201      JP HUGH
133:   00FA FEF6        CPI -10
134:   00FC FA1901      JM LEW
135:   00FF C32B01      JMP OK;TARGET OK SO GO ON
136:   0102 3A0640      HUGH LDA VOLT;LEG NEEDS LESS VOLTS
137:   0105 C600        ADI 00
138:   0107 FA0F01      JM LW1
```

```
139:    010A FE0A       CPI 10
140:    010C FA2B01     JM OK
141:    010F D601   LW1 SUI 01
142:    0111 320640     STA VOLT
143:    0114 D380       OUT DA
144:    0116 C32B01     JMP OK
145:    0119 3A0640 LEW LDA VOLT;LEG NEEDS MORE VOLTS
146:    011C FEFA       CPI 250
147:    011E CA3702     JZ STOP
148:    0121 C601       ADI 01
149:    0123 320640     STA VOLT
150:    0126 D380       OUT DA
151:    0128 C32B01     JMP OK
152:    012B D3E6    OK OUT STROBE6;
HOT ENTRY FOR NO CHANGE IN STIM VOLTS
153:    012D CD0902     CALL DELAY
154:    0130 DBE6       IN AD6
155:    0132 C600       ADI 00
156:    0134 F23C01     JP EE;CHECK FOR HYPER EXTENSION
157:    0137 D601       SUI 01
158:    0139 FA3702     JM STOP;KNEE HYPEREXTENDED GET OUT
159:    013C D3E5    EE OUT STROBE5
160:    013E CD0902     CALL DELAY
161:    0141 DBE5       IN AD5
162:    0143 FE78       CPI 120
163:    0145 CA4B01     JZ OK1
164:    0148 C3D900     JMP TAG2;LOOP IF NOT AT RAMP TOP
165:
166:
167:
168:
169:                    ;CHECK WEIGHT AND TEMP AND HR
170:
171:
172:
173:    014B 3AFF06 OK1 LDA 06FFH;CHECK FOR DIVER LOAD RANGE
174:    014E 320440     STA STORE1
175:    0151 3A0F06     LDA 060 FH
176:    0154 E601       ANI 01
177:    0156 C26401     JNZ OK2
178:    0159 3A0F06  K4 LDA 060 FH
179:    015C E604       ANI 04
180:    015E C27001     JNZ OK4
181:    0161 C37901     JMP OK5
182:    0164 3AF406 OK2 LDA 06F4H
183:    0167 320440     STA STORE1
184:    016A CD2402     CALL HR
185:    016D C35901     JMP K4
186:    0170 3AF806 OK4 LDA 06F8H
187:    0173 320440     STA STORE1
188:    0176 CD1102     CALL TEMP
189:
190:
191:
192:
193:    0179 D3E5   OK5 OUT STROBE5;
```

```
GO ON WITH DOWN RAMP TO LOWER LEG
194:   017B CD0902      CALL DELAY
195:   017E CD0902      CALL DELAY
196:   0181 CD0902      CALL DELAY
197:   0184 DBE5        IN AD5
198:   0186 47          MOV B,A
199:   0187 D3E6        OUT STROBE6
200:   0189 CD0902      CALL DELAY
201:   018C CD0902      CALL DELAY
202:   018F CD0902      CALL DELAY
203:   0192 DBE6        IN AD6
204:   0194 90          SUB B;LEG POSITION-RAMP
205:   0195 FE0A        CPI 10
206:   0197 F2A201      JP HIGH10
207:   019A FEF6        CPI -10
208:   019C FAB901      JM LOW10
209:   019F C3CB01      JMP OK10
210:   01A2 3A0640      HIGH10 LDA VOLT
211:   01A5 C600        ADI 00
212:   01A7 FAAF01      JM LE10
213:   01AA FE0A        CPI 10
214:   01AC FACB01      JM OK10
215:   01AF D601        LE10 SUI 01
216:   01B1 320640      STA VOLT
217:   01B4 D380        OUT DA
218:   01B6 C3CB01      JMP OK10
219:   01B9 3A0640      LOW10 LDA VOLT
220:   01BC FEFA        CPI 250
221:   01BE CA3702      JZ STOP
222:   01C1 C601        ADI 01
223:   01C3 320640      STA VOLT
224:   01C6 D380        OUT DA
225:   01C8 C3CB01      JMP OK10
226:
227:
228:
229:   01CB D3E5        OK10 OUT STROBES
230:   01CD CD0902      CALL DELAY
231:   01D0 DBE5        IN AD5
232:   01D2 FE05        CPI 05
233:   01D4 F27901      JP OK5
234:
235:
236:
237:
238:
239:
240:   01D7 3A0506      LDA 0605H
241:   01DA E602        ANI 02
242:   01DC F2E201      JP L4
243:   01DF C3F101      JMP L5
244:   01E2 3AF506      L4 LDA 06F5H
245:   01E5 320440      STA STORE1
246:   01E8 3AF706      LDA 06F7H
247:   01EB 320540      STA STORE2
248:   01EE CDB702      CALL BP
```

```
249:   01F1 3E01      L5 MVI A,01
250:   01F3 67           MOV H,A
251:   01F4 6F           MOV L,A
252:   01F5 2C        L7 INR L
253:   01F6 7C           MOV A,H
254:   01F7 C600         ADI 00
255:   01F9 CAFF01       JZ L6
256:   01FC C3F501       JMP L7
257:   01FF C3B500    L6 JMP TAG1;LOOP BACK
258:
259:   0202 3E40      OVER MVI A,40H
260:   0204 D380         OUT PORT
261:   0206 C30202       JMP OVER
262:
263:
264:
265:
266:                  ;          CONSTANTS
267:   00E0 =         STROBE0 EQU 0E0H
268:   00E1 =         STROBE1 EQU 0E1H
269:   0080 =         PORT EQU 080H
270:   00E2 =         STROBE2 EQU 0E2H
271:   00E3 =         STROBE3 EQU 0E3H
272:   00E4 =         STROBE4 EQU 0E4H
273:   00E5 =         STROBE5 EQU 0E5H
274:   00E6 =         STROBE6 EQU 0E6H
275:   00E7 =         STROBE7 EQU 0E7H
276:
277:
278:   0080 =         DA EQU 080H
279:   00F0 =         PORT1 EQU 0F0H
280:
281:
282:   00E0 =         AD0 EQU 0E0H
283:   00E1 =         AD1 EQU 0E1H
284:   00E2 =         AD2 EQU 0E2H
285:   00E3 =         AD3 EQU 0E3H
286:   00E4 =         AD4 EQU 0E4H
287:   00E5 =         AD5 EQU 0E5H
288:   00E6 =         AD6 EQU 0E6H
289:   00E7 =         AD7 EQU 0E7H
290:
291:
292:
293:                  ;          DELAY ROUTINE
294:
295:   0209 3E7F      DELAY MVI A,127
296:   020B C601      DELAY1 ADI 01
297:   020D C20B02       JNZ DELAY1
298:   0210 C9           RET
299:
300:
301:
302:                  ;          TEMP LIMIT
303:
304:
```

```
305:   0211 D3E1      TEMP OUT STROBE1
306:   0213 CD0902    CALL DELAY
307:   0216 DBE1      IN AD1
308:   0218 47        MOV B,A
309:   0219 320340    STA TEMPS
310:   021C 3A0440    LDA STORE1
311:   021F 90        SUB B
312:   0220 FA3702    JM STOP
313:   0223 C9        RET
314:
315:
316:
317:                  ;       HEART RATE LIMIT
318:
319:
320:   0224 D3E2      HR OUT STROBE2
321:   0226 CD0902    CALL DELAY
322:   0229 DBE2      IN AD2
323:   022B 47        MOV B,A
324:   022C 320240    STA HER
325:   022F 3A0440    LDA STORE1
326:   0232 90        SUB B
327:   0233 FA3702    JM STOP
328:   0236 C9        RET
329:
330:
331:
332:
333:                  ;            STOP PROGRAM
334:
335:
336:   0237 3EFF      STOP MVI A,255
337:   0239 D380      OUT PORT
338:   023B 3E00      MVI A,00
339:   023D D380      OUT DA
340:   023F 3AF606    LDA 06F6H
341:   0242 6F        MOV L,A
342:   0243 3E07      MVI A,07H
343:   0245 67        MOV H,A
344:   0246 3A0740    LDA COUNT
345:   0249 77        MOV M,A
346:   024A 3E7D      MVI A,125
347:   024C 320440    STA STORE1
348:   024F 320540    STA STORE2
349:   0252 CDB702    CALL BP
350:   0255 3E30      MVI A,30H
351:   0257 85        ADD L
352:   0258 6F        MOV L,A
353:   0259 3A0040    LDA SYSTOLIC
354:   025C 77        MOV M,A
355:   025D CD0902    CALL DELAY
356:   0260 3E10      MVI A,10H
357:   0262 85        ADD L
358:   0263 6F        MOV L,A
359:   0264 3A0140    LDA DIASTOLIC
360:   0267 77        MOV M,A
```

```
361:    0268 CD0902       CALL DELAY
362:    026B 3AF606       LDA 06F6H
363:    026E C601         ADI 01
364:    0270 32F606       STA 06F6H
365:    0273 CD0902       CALL DELAY
366:    0276 3AF606       LDA 06F6H
367:    0279 D601         SUI 01
368:    027B C610         ADI 10H
369:    027D 6F           MOV L,A
370:    027E D3E2         OUT STROBE2
371:    0280 CD0902       CALL DELAY
372:    0283 DBE2         IN AD2
373:    0285 77           MOV M,A
374:    0286 CD0902       CALL DELAY
375:    0289 CD0902       CALL DELAY
376:    028C 3AF606       LDA 06F6H
377:    028F D601         SUI 01
378:    0291 C670         ADI 70H
379:    0293 6F           MOV L,A
380:    0294 D3E1         OUT STROBE1
381:    0296 CD0902       CALL DELAY
382:    0299 DBE1         IN AD1
383:    029B 77           MOV M,A
384:    029C CD0902       CALL DELAY
385:    029F 3E00         MVI A,00
386:    02A1 D380         OUT DA
387:    02A3 00           JOB NOP
388:    02A4 C3A302       JMP JOB
389:                      ; END
390:
391:
392:
393:
394:
395:
396:
397:
398:
399:    02A7 D3E0         WEIGHT OUT STROBE0
400:    02A9 CD0902       CALL DELAY
401:    02AC DBE0         IN AD0
402:    02AE 47           MOV B,A
403:    02AF 3A0440       LDA STORE1
404:    02B2 90           SUB B
405:    02B3 FA3702       JM STOP
406:    02B6 C9           RET
407:
408:
409:
410:
411:
412:                      ;     BP CHECK SUBROUTINE
413:
414:    02B7 D3E4         BP OUT STROBE4
415:    02B9 CD0902       CALL DELAY
416:    02BC DBE4         IN AD4
```

```
417:    02BE FEFA          CPI 250
418:    02C0 C2B702        JNZ BP
419:    02C3 D3E3      BP1 OUT STROBE3
420:    02C5 CD0902        CALL DELAY
421:    02C8 DBE3          IN AD3
422:    02CA FE32          CPI 50
423:    02CC FAC302        JM BP1
424:    02CF D3E4          OUT STROBE4
425:    02D1 CD0902        CALL DELAY
426:    02D4 DBE4          IN AD4
427:    02D6 320040        STA SYSTOLIC
428:    02D9 D3E3      BP2 OUT STROBE3
429:    02DB CD0902        CALL DELAY
430:    02DE DBE3          IN AD3
431:    02E0 C600          ADI 00
432:    02E2 FAD902        JM BP2
433:    02E5 FE14          CPI 20
434:    02E7 F2D902        JP BP2
435:    02EA D3E4          OUT STROBE4
436:    02EC CD0902        CALL DELAY
437:    02EF DBE4          IN AD4
438:    02F1 320140        STA DIASTOLIC
439:    02F4 3A0040        LDA SYSTOLIC
440:    02F7 47            MOV B,A
441:    02F8 3A0440        LDA STORE1
442:    02FB 90            SUB B
443:    02FC FA3702        JM STOP
444:    02FF 3A140         LDA DIASTOLIC
445:    0302 47            MOV B,A
446:    0303 3A0540        LDA STORE2
447:    0306 90            SUB B
448:    0307 FA3702        JM STOP
449:    030A C9            RET
450:
451:
452:
453:
454:
455:
456:    4000               ORG 4000H
457:    4000 00            SYSTOLIC NOP
458:    4001 00            DIASTOLIC NOP
459:    4002 00            HER NOP
460:    4003 00            TEMPS NOP
461:    4004 00            STORE1 NOP
462:    4005 00            STORE2 NOP
463:    4006 00            VOLT NOP
464:    4007 00            COUNT NOP
```

What is claimed is:

1. Method of exercising a limb of a specific human individual comprising the steps of:

storing in a portable electronically readable memory control instructions for a specifically prescribed exercise routine and a plurality of physiological parameters corresponding to specifically prescribed limits on the physiological response of said human individual to said exercise routine, placing said memory into communication with an exercise control device, causing said exercise control device to read said exercise control instructions from said memory and generate a series of stimulation signals in response thereto, producing coordinated repetitive movement of said limb by applying said stimulation signals to muscles connected for production of said movement, measuring the physiological response of said human individual to said movement, causing said exercise control device to read said physiological parameters from said memory, and terminating the generation of said stimulation signals when said physiological response exceeds any of said prescribed limits.

2. Method according to claim 1 and comprising the further steps of:

storing in said memory a use count corresponding to a prescribed maximum usage thereof, modifying said use count when the generation of said stimulation signals has been terminated as aforesaid, following modification of said use count, comparing the modified count against a predetermined count, repeating the operation of said exercise control device if and only if said comparison of said modified count against said predetermined count indicates that said prescribed maximum usage has not been reached.

3. Method according to claim 2 and comprising the further steps of:

storing in said memory a number corresponding to a prescribed maximum number of repetitions of said movement, counting the number of repetitions of said movement, and terminating the generation of said stimulation signals when said maximum number of repetitions has been reached.

4. Method according to claim 3, wherein said exercise control instructions comprise an instruction setting forth a prescribed maximum load; said method further comprising the steps of:

applying a load against said limb to resist movement thereof, measuring said load, and preventing generation of said stimulation signals if said load measurement indicates that said prescribed maximum load has been exceeded.

5. Method according to claim 3 and comprising the further steps of:

generating a reference signal representing a desired movement pattern for said limb, measuring the actual movement of said limb, comparing the actual movement of said limb against the desired movement represented by said reference signal, and adjusting said stimulation signals in correspondence with the difference between said actual movement and said desired movement.

6. Method of prescribing an exercise routine for a paralyzed limb of a specific human individual comprising the steps of:

storing instructions for the conduct of said routine in a computer memory, storing in said computer memory a plurality of specifically established physiological parameters setting forth prescribed limits on the physiogicl response of said human individual to said routine, copying said instructions and said physiological parameters from said computer memory into an electronically programmable memory cartridge, and storing in said cartridge a count for controlling the number of uses thereof.

7. Apparatus for exercising a limb of a specific human individual comprising:

stimulation means for stimulating a predetermined movement of said limb, a response sensor for sensing physiological response to said movement, an exercise control device for enabling cyclical repetitive operation of said stimulation means and terminating said operation when said physiological response reaches a predetermined limit, a programmable memory cartridge loaded with information specifically establishing said limit for said human individual, and connector means for releasably connecting said cartridge to said exercise control device and enabling said exercise control device to read said specifically established information.

8. Apparatus according to claim 7 wherein said response sensor senses body temperature.

9. Apparatus according to claim 8 and further comprising a second sensor for sensing blood pressure and a third sensor for sensing heart rate; said memory cartridge being loaded with information corresponding to a predetermined maximum blood pressure and a predetermined maximum heart rate; said exercise control device being connected for reading said maximum blood pressure and said maximum heart rate and terminating operation of said stimulation means when either of said blood pressure or said heart rate reaches its corresponding predetermined maximum value.

10. Apparatus according to claim 7 wherein said limb is a leg, said stimulation means are connected for stimulating lifting of said leg and said exercise control device comprises load means for generating a load to resist said lifting.

11. Apparatus according to claim 10 wherein said memory cartridge is loaded with information corresponding to a predetermined maximum level for said load; said exercise control device comprising means for reading said predetermined maximum load level, load cell means for determining the actual level of said load and comparing means for comparing said actual level against said predetermined maximum level.

12. Apparatus according to claim 10 wherein said exercise control device further comprises:

means for generating a reference signal representing a desired lifting pattern for said leg, means for measuring the actual lifting of said leg, means for comparing the actual lifting of said leg against the desired lifting represented by said reference signal, and means for controlling the operation of said stimulation means in correspondence with the difference between said actual lifting and said desired lifting.

* * * * *